(12) United States Patent
Hoefle et al.

(10) Patent No.: US 6,624,310 B1
(45) Date of Patent: Sep. 23, 2003

(54) EPOTHILONE MINOR CONSTITUENTS

(75) Inventors: Gerhard Hoefle, Braunschweig (DE); Hans Reichenbach, Braunschweig (DE); Klaus Gerth, Braunschweig (DE); Ingo Hardt, Braunschweig (DE); Florenz Sasse, Braunschweig (DE); Heinrich Steinmetz, Braunschweig (DE)

(73) Assignee: Gesellschaft fuer Biotechnologische Forschung, mbH (GBF), Braunschweig (DE)

( * ) Notice: Subject to any disclaimer, the term of this patent is extended or adjusted under 35 U.S.C. 154(b) by 0 days.

(21) Appl. No.: 09/719,932

(22) PCT Filed: Jun. 18, 1999

(86) PCT No.: PCT/EP99/04244

§ 371 (c)(1),
(2), (4) Date: Mar. 21, 2001

(87) PCT Pub. No.: WO99/65913

PCT Pub. Date: Dec. 23, 1999

(30) Foreign Application Priority Data

Jun. 18, 1998 (DE) .......................... 198 26 988

(51) Int. Cl.⁷ ............................ C07D 493/04
(52) U.S. Cl. .................................... 548/204
(58) Field of Search .......................... 548/204

(56) References Cited

FOREIGN PATENT DOCUMENTS

| | | |
|---|---|---|
| WO | WO 97/19086 | 5/1997 |
| WO | WO 98/08849 | 3/1998 |
| WO | WO 98/22461 | 5/1998 |
| WO | WO 98/25929 | 6/1998 |
| WO | WO 99/01124 | 1/1999 |
| WO | WO 99/02514 | 1/1999 |
| WO | WO 99/07692 | 2/1999 |
| WO | WO 99/27890 | 6/1999 |
| WO | WO 99/43653 | 9/1999 |
| WO | WO 99/54319 | 10/1999 |
| WO | WO 00/00485 | 1/2000 |
| WO | WO 00/31247 | 6/2000 |
| WO | WO 00/49012 | 8/2000 |
| WO | WO 98/25929 | 11/2002 |

OTHER PUBLICATIONS

Nicolaou et al., 1998, "Chemical Biology of Epothilones", Angew. Chem. Int. Ed. 37:2014–2045.

*Primary Examiner*—Robert Gerstl
(74) *Attorney, Agent, or Firm*—Rena Patel; Pennie & Edmonds LLP

(57) ABSTRACT

The invention relates to compounds which are obtained by fermenting DSM 6773, especially epothilones A1, A2, A8, A9, B10, C1, C2, C3, C4, C5, C6, C7, C8, C9, D1, D2, D5, G1, G2, H1, H2, I1, I2, I3, I4, I5, I6 and K and trans-epothilones C1 and C2.

1 Claim, 2 Drawing Sheets

Fig. 2

Figure 1:
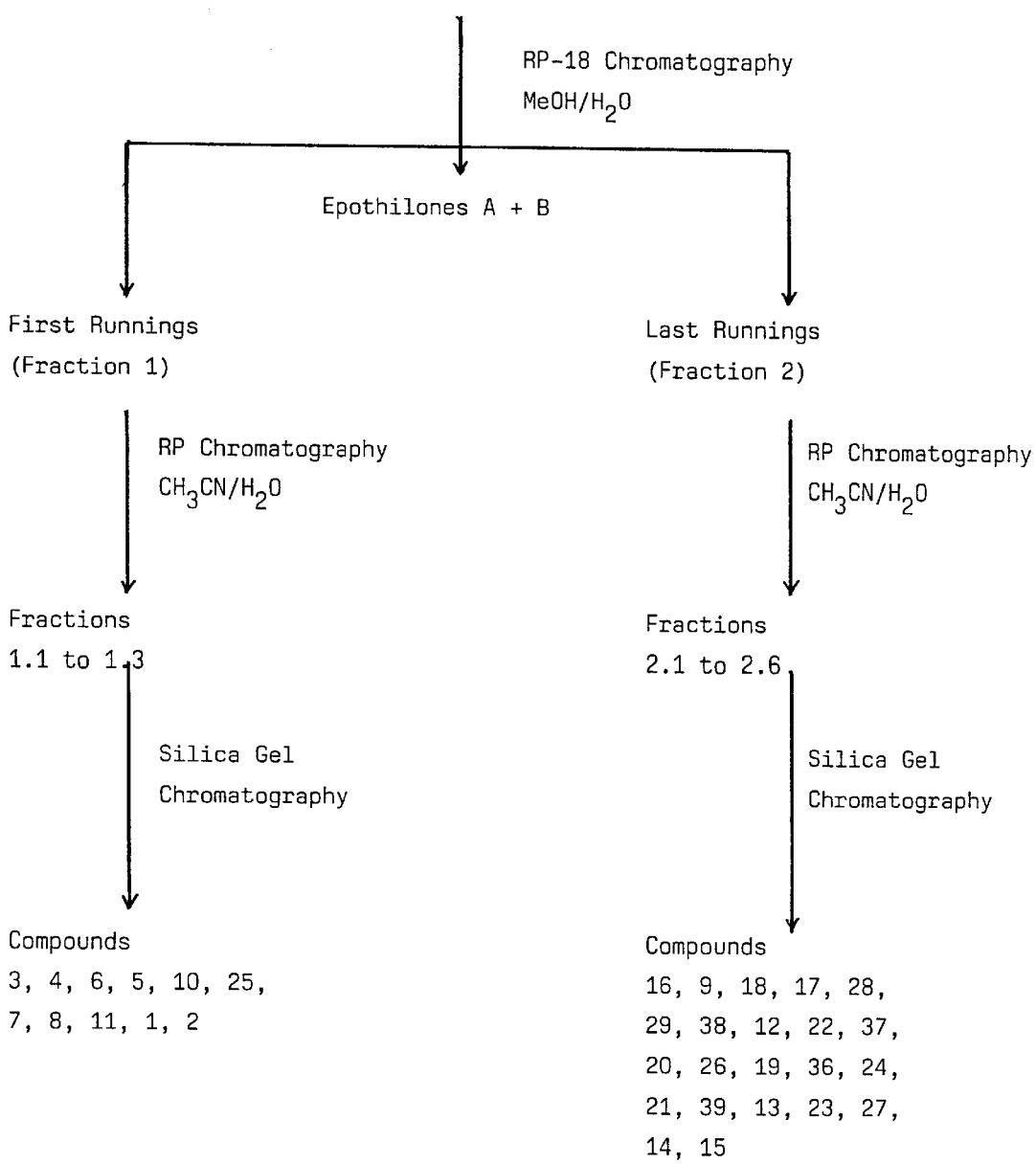

| | | Compound | Amount |
|---|---|---|---|
| | | Epothilone E (3) | variable[a] |
| | | Epothilone F (4) | variable[a] |
| fraction 1 | 1.1 | Epothilone A₂ (6) | 14.5 mg |
| | | Epothilone A₁ (5) | 3.1 mg |
| | | Epothilone G₁ (10) | 52.3 mg |
| | | Epothilone C₇ (25) | 0.9 mg |
| | 1.2 | Epothilone A₈ (7) | 38.7 mg |
| | | Epothilone A₉ (8) | 4.4 mg |
| | 1.3 | Epothilone G₂ (11) | 9.4 mg |
| | | Epothilone A (1) | 29800.0 mg |
| | | Epothilone B (2) | 10300.0 mg |
| fraction 2 | 2.1 | Epothilone C₁ (16) | 32.4 mg |
| | | Epothilone B₁₀ (9) | 1.1 mg |
| | 2.2 | Epothilone C₂ (18) | 58.4 mg |
| | 2.3 | Epothilone D₁ (17) | 5.3 mg |
| | | trans-Epothilone C₁ (28) | 1.4 mg |
| | | trans-Epothilone C₂ (29) | 4.5 mg |
| | | 38 | 6.5 mg |
| | | Epothilone H₁ (12) | 3.0 mg |
| | | Epothilone C₅ (22) | 7.3 mg |
| | 2.4 | 37 | 2.9 mg |
| | | Epothilone C₃ (20) | 32.5 mg |
| | | Epothilone C₆ (26) | 26.3 mg |
| | 2.5 | Epothilone D₂ (19) | 13.1 mg |
| | | Epothilone K (36) | 0.4 mg |
| | | Epothilone C₈ (24) | 2.9 mg |
| | | Epothilone C₄ (21) | 6.5 mg |
| | 2.6 | 39 | 0.8 mg |
| | | Epothilone H₂ (13) | 1.5 mg |
| | | Epothilone D₅ (23) | 0.9 mg |
| | | Epothilone C₉ (27) | 3.0 mg |
| | | Epothilone C (14) | 4600.0 mg |
| | | Epothilone D (15) | 2700.0 mg |

EPOTHILONE MINOR CONSTITUENTS

The invention concerns compounds which in the present context are designated epothilone side components, viz. compounds 5 to 13 and 16 to 39. These compounds can be produced by fermenting DSM 6773 in accordance to DE 41 38 042.8.

Characterizing data of the compounds according to the invention will be compiled as follows.

Production: The processing of a raw epothilone mixture, which has been produced by fermenting DSM 6773 in a 900 l fermentor, can be drawn schematically from FIGS. 1 to 2.

Activities: cf. table 1

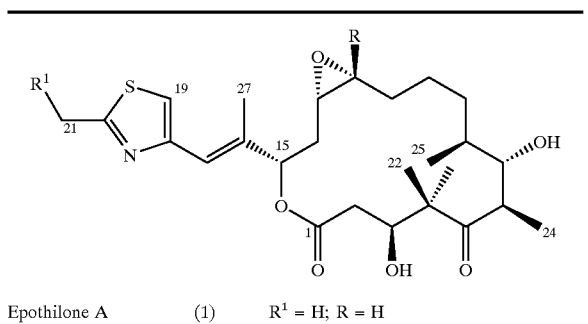

| Epothilone A | (1) | $R^1$ = H; R = H |
| Epothilone B | (2) | $R^1$ = H; R = Me |
| Epothilone E | (3) | $R^1$ = OH, R = H |
| Epothilone F | (4) | $R^1$ = OH; R = Me |

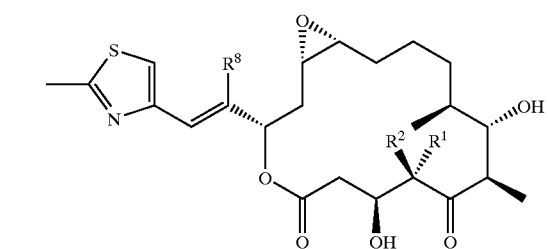

| Epothilone $A_1$ | (5) | $R^1$ = H; $R^2$, $R^8$ = Me |
| Epothilone $A_2$ | (6) | $R^2$ = H; $R^1$, $R^8$ = Me |
| Epothilone $A_8$ | (7) | $R^8$ = H; $R^1$, $R^2$ = Me |
| Epothilone $A_9$ | (8) | $R^1$ = $CH_2OH$; $R^2$, $R^8$ = Me |

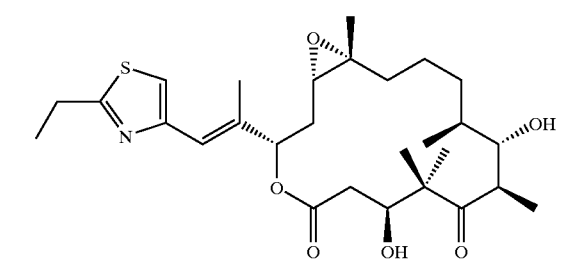

Epothilone $B_{10}$  (9)

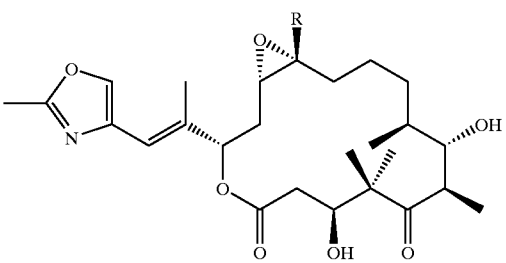

| Epothilone $G_1$ | (10) | R = H |
| Epothilone $G_2$ | (11) | R = Me |

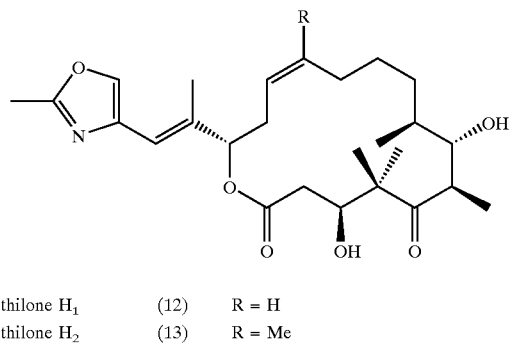

| Epothilone $H_1$ | (12) | R = H |
| Epothilone $H_2$ | (13) | R = Me |

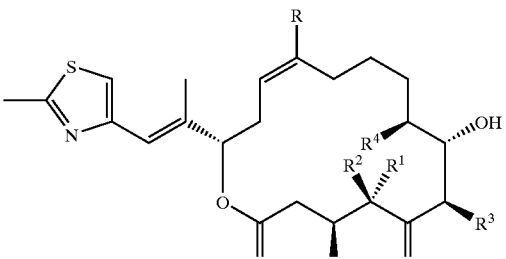

| Epothilone C | (14) | $R^1$, $R^2$, $R^3$, $R^4$ = Me; R = H |
| Epothilone D | (15) | $R^1$, $R^2$, $R^3$, $R^4$, R = Me |
| Epothilone $C_1$ | (16) | $R^1$ = H; $R^2$, $R^3$, $R^4$ = Me; R = H |
| Epothilone $D_1$ | (17) | $R^1$ = H; $R^2$, $R^3$, $R^4$ = Me; R = Me |
| Epothilone $C_2$ | (18) | $R^2$ = H; $R^1$, $R^3$, $R^4$ = Me; R = H |
| Epothilone $D_2$ | (19) | $R^2$ = H; $R^1$, $R^3$, $R^4$ = Me; R = Me |
| Epothilone $C_3$ | (20) | $R^3$ = H; $R^1$, $R^2$, $R^4$ = Me; R = H |
| Epothilone $C_4$ | (21) | $R^4$ = H; $R^1$, $R^2$, $R^3$ = Me; R = H |

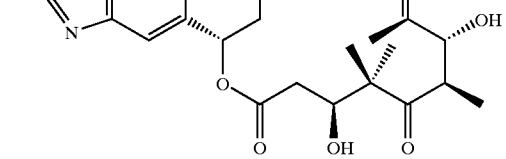

| Epothilone $C_5$ | (22) | R = H |
| Epothilone $D_5$ | (23) | R = Me |

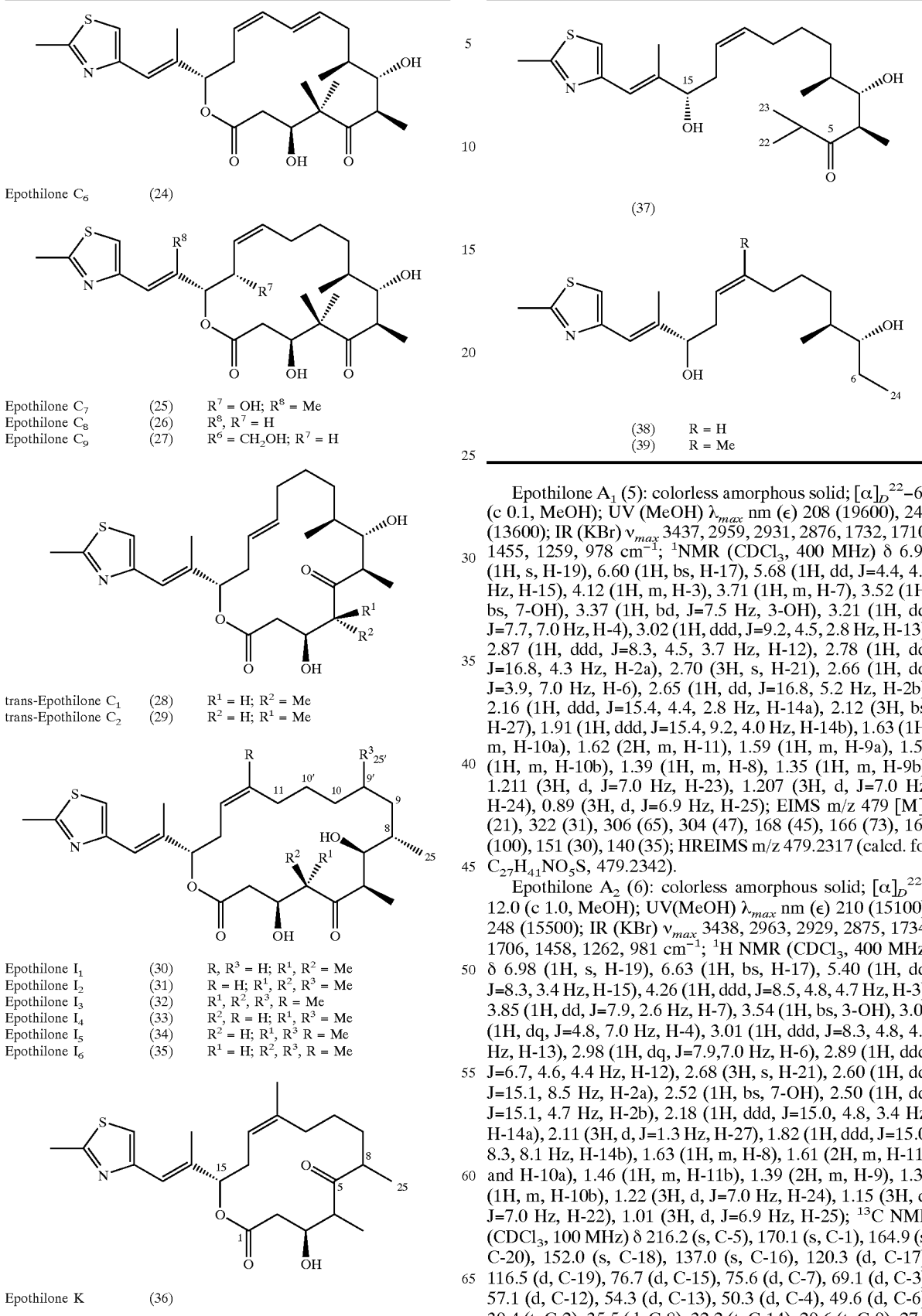

Epothilone C₆ (24)

Epothilone C₇ (25) R⁷ = OH; R⁸ = Me
Epothilone C₈ (26) R⁸, R⁷ = H
Epothilone C₉ (27) R⁶ = CH₂OH; R⁷ = H trans-Epothilone C₁ (28) R¹ = H; R² = Me
trans-Epothilone C₂ (29) R² = H; R¹ = Me Epothilone I₁ (30) R, R³ = H; R¹, R² = Me
Epothilone I₂ (31) R = H; R¹, R², R³ = Me
Epothilone I₃ (32) R¹, R², R³, R = Me
Epothilone I₄ (33) R², R = H; R¹, R³ = Me
Epothilone I₅ (34) R² = H; R¹, R³ R = Me
Epothilone I₆ (35) R¹ = H; R², R³, R = Me Epothilone K (36)

(37)

(38) R = H
(39) R = Me

Epothilone $A_1$ (5): colorless amorphous solid; $[\alpha]_D^{22}$ −69 (c 0.1, MeOH); UV (MeOH) $\lambda_{max}$ nm ($\epsilon$) 208 (19600), 247 (13600); IR (KBr) $\nu_{max}$ 3437, 2959, 2931, 2876, 1732, 1710, 1455, 1259, 978 cm⁻¹; ¹NMR (CDCl₃, 400 MHz) δ 6.95 (1H, s, H-19), 6.60 (1H, bs, H-17), 5.68 (1H, dd, J=4.4, 4.0 Hz, H-15), 4.12 (1H, m, H-3), 3.71 (1H, m, H-7), 3.52 (1H, bs, 7-OH), 3.37 (1H, bd, J=7.5 Hz, 3-OH), 3.21 (1H, dq, J=7.7, 7.0 Hz, H-4), 3.02 (1H, ddd, J=9.2, 4.5, 2.8 Hz, H-13), 2.87 (1H, ddd, J=8.3, 4.5, 3.7 Hz, H-12), 2.78 (1H, dd, J=16.8, 4.3 Hz, H-2a), 2.70 (3H, s, H-21), 2.66 (1H, dq, J=3.9, 7.0 Hz, H-6), 2.65 (1H, dd, J=16.8, 5.2 Hz, H-2b), 2.16 (1H, ddd, J=15.4, 4.4, 2.8 Hz, H-14a), 2.12 (3H, bs, H-27), 1.91 (1H, ddd, J=15.4, 9.2, 4.0 Hz, H-14b), 1.63 (1H, m, H-10a), 1.62 (2H, m, H-11), 1.59 (1H, m, H-9a), 1.52 (1H, m, H-10b), 1.39 (1H, m, H-8), 1.35 (1H, m, H-9b), 1.211 (3H, d, J=7.0 Hz, H-23), 1.207 (3H, d, J=7.0 Hz, H-24), 0.89 (3H, d, J=6.9 Hz, H-25); EIMS m/z 479 [M]⁺ (21), 322 (31), 306 (65), 304 (47), 168 (45), 166 (73), 164 (100), 151 (30), 140 (35); HREIMS m/z 479.2317 (calcd. for $C_{27}H_{41}NO_5S$, 479.2342).

Epothilone $A_2$ (6): colorless amorphous solid; $[\alpha]_D^{22}$+ 12.0 (c 1.0, MeOH); UV(MeOH) $\lambda_{max}$ nm ($\epsilon$) 210 (15100), 248 (15500); IR (KBr) $\nu_{max}$ 3438, 2963, 2929, 2875, 1734, 1706, 1458, 1262, 981 cm⁻¹; ¹H NMR (CDCl₃, 400 MHz) δ 6.98 (1H, s, H-19), 6.63 (1H, bs, H-17), 5.40 (1H, dd, J=8.3, 3.4 Hz, H-15), 4.26 (1H, ddd, J=8.5, 4.8, 4.7 Hz, H-3), 3.85 (1H, dd, J=7.9, 2.6 Hz, H-7), 3.54 (1H, bs, 3-OH), 3.09 (1H, dq, J=4.8, 7.0 Hz, H-4), 3.01 (1H, ddd, J=8.3, 4.8, 4.6 Hz, H-13), 2.98 (1H, dq, J=7.9,7.0 Hz, H-6), 2.89 (1H, ddd, J=6.7, 4.6, 4.4 Hz, H-12), 2.68 (3H, s, H-21), 2.60 (1H, dd, J=15.1, 8.5 Hz, H-2a), 2.52 (1H, bs, 7-OH), 2.50 (1H, dd, J=15.1, 4.7 Hz, H-2b), 2.18 (1H, ddd, J=15.0, 4.8, 3.4 Hz, H-14a), 2.11 (3H, d, J=1.3 Hz, H-27), 1.82 (1H, ddd, J=15.0, 8.3, 8.1 Hz, H-14b), 1.63 (1H, m, H-8), 1.61 (2H, m, H-11a and H-11b), 1.46 (1H, m, H-10a), 1.39 (2H, m, H-9), 1.31 (1H, m, H-10b), 1.22 (3H, d, J=7.0 Hz, H-24), 1.15 (3H, d, J=7.0 Hz, H-22), 1.01 (3H, d, J=6.9 Hz, H-25); ¹³C NMR (CDCl₃, 100 MHz) δ 216.2 (s, C-5), 170.1 (s, C-1), 164.9 (s, C-20), 152.0 (s, C-18), 137.0 (s, C-16), 120.3 (d, C-17), 116.5 (d, C-19), 76.7 (d, C-15), 75.6 (d, C-7), 69.1 (d, C-3), 57.1 (d, C-12), 54.3 (d, C-13), 50.3 (d, C-4), 49.6 (d, C-6), 39.4 (t, C-2), 35.5 (d, C-8), 32.2 (t, C-14), 29.6 (t, C-9), 27.6

(t, C-11), 23.9 (t, C-10), 19.2 (q, C-21), 18.0 (q, C-25), 15.6 (q, C-27), 13.9 (q, C-24), 12.4 (q, C-22); EIMS m/z 479 [M]⁺ (18), 322 (38), 306 (78), 304 (59), 168 (48), 166 (96), 164 (100), 151 (33), 140 (38); HREIMS m/z 479.2318 (calcd. for $C_{27}H_{41}NO_5S$, 479.2342).

Epothilone $A_8$ (7): colorless amorphous solid; $[\alpha]_D^{22}$ −76.2 (c 1.0, MeOH); UV (MeOH) $\lambda_{max}$ nm ($\epsilon$) 210 (15300), 248 (15500); IR (KBr) $\nu_{max}$ 3440, 2967, 2932, 2876, 1736, 1691, 1467, 1252, 979 cm⁻¹; ¹H NMR (CDCl₃, 400 MHz) δ 6.95 (1H, s, H-19), 6.64 (1H, dd, J=15.6, 0.9 Hz, H-17), 6.52 (1H, dd, J=15.6, 6.6 Hz, H-16), 5.68 (1H, dddd, J=7.8, 6.6, 3.2, 0.9 Hz, H-15), 4.11 (1H, ddd, J=10.1, 6.6, 3.5 Hz, H-3), 3.78 (1H, ddd, J=5.2, 3.2, 3.2 Hz, H-7), 3.66 (1H, d, J=6.6 Hz, 3-OH), 3.23 (1H, dq, J=5.2, 6.9 Hz, H-6), 3.08 (1H, ddd, J=7.3, 5.5, 4.1 Hz, H-13), 2.90(1H, ddd, J=6.6, 4.6, 4.1 Hz, H-12), 2.69 (3H, s, H-21), 2.52 (1H, dd, J=14.7, 10.1 Hz, H-2a), 2.44 (1H, bd, J=3.2 Hz, 7-OH), 2.41 (1H, dd, J=14.7, 3.5 Hz, H-2b), 2.10 (1H ddd, J=15.0, 5.5, 3.2 Hz, H-14a), 1.90 (1H, ddd, J=15.0, 7.8, 7.3 Hz, H-14b), 1.71 (1H, m, H-8), 1.65 (1H, m, H-11a), 1.50 (1H, m, H-10a), 1.47 (1H, m, H-11b), 1.40 (2H, m, H-9), 1.39 (1H, m, H-10b), 1.33 (3H, s, H-23), 1.16 (3H, d, J=6.9 Hz, H-24), 1.08 (3H, s, H-22), 0.98 (3H, d, J=7.0 Hz, H-25); ¹³C NMR (CDCl₃, 75 MHz) δ 220.3 (s, C-5), 170.7 (s, C-1), 166.5 (s, C-20), 152.2 (s, C-18), 128.4 (d, C-16), 125.9 (d, C-17), 116.4 (d, C-19), 75.0 (d, C-7), 73.6 (d, C-3), 72.7 (d, C-15), 57.3 (d, C-12), 54.1 (d, C-13), 52.6 (s, C-4), 43.8 (d, C-6), 38.9 (t, C-2), 36.3 (d, C-8), 32.5 (t, C-14), 30.3 (t, C-9), 26.7 (t, C-11), 24.0 (t, C-10), 21.3 (q, C-23), 21.0 (q, C-22), 19.3 (q, C-21), 17.1 (q, C-25), 14.5 (q, C-24); EIMS m/z 479 [M]⁺ XXX; HRDCIMS m/z 480.2401 (calcd. for $C_{25}H_{38}NO_6S$, 480.2401).

Epothilone $A_9$ (8): colorless amorphous solid; $[\alpha]_D^{22}$ −37.6 (c 0.5, MeOH); UV (MeOH) $\lambda_{max}$ nm ($\epsilon$) 211 (15500), 253 (14100); IR (KBr) $\nu_{max}$ 3423, 2965, 2932, 2877, 1736, 1690, 1463, 1249, 1014, 979 cm⁻¹; ¹H NMR (CDCl₃, 400 MHz) δ 7.10 (1H, s, H-19), 6.72 (1H, dd, J=10.7, 4.3 Hz, 27-OH), 6.60 (1H, bs, H-17), 5.69 (1H, dd, J=11.6, 2.0 Hz, H-15), 5.59 (1H, d, J=6.6 Hz, 3-OH), 4.49 (1H, ddd, J=12.9, 4.3, 1.2 Hz, H-27a), 4.27 (1H, ddd, J=11.6, 6.6, 2.9 Hz, H-3), 4.11 (1H, ddd, J=12.9, 10.7, 1.0 Hz, H-27b), 3.71 (1H, ddd, J=4.8, 3.0, 2.8 Hz, H-7), 3.17 (1H, dq, J=3.0, 6.8 Hz, H-6), 3.04 (1H, ddd, J=9.7, 3.6, 2.2 Hz, H-13), 2.93 (1H, bs, 7-OH), 2.91 (1H, ddd, J=9.7, 3.6, 2.7 Hz, H-12), 2.72 (3H, s, H-21), 2.48 (1H, dd, J=14.2, 11.6 Hz, H-2a), 2.11 (1H, dd, J=14.2, 2.9 Hz, H-2b), 2.03 (1H, ddd, J=14.7, 2.2, 2.0 Hz, H-14a), 1.86 (1H, m, H-11a), 1.85 (1H, m, H-14b), 1.79 (1H, m, H-8), 1.52 (1H, m, H-10a), 1.37 (3H, m, H-9 and H-10b), 1.37 (3H, s, H-23), 1.36 (1H, m, H-11b), 1.19 (3H, d, J=6.8 Hz, H-24), 1.02 (3H, d, J=7.1 Hz, H-25), 1.00 (3H, s, H-22); ¹³C NMR (CDCl₃, 75 MHz) δ 220.5 (s, C-5), 170.2 (s, C-1), 167.5 (s, C-20), 150.7 (s, C-18), 138.9 (s, C-16), 125.2 (d, C-17), 119.5 (d, C-19), 76.7 (d, C-15), 73.4 (d, C-7), 70.4 (d, C-3), 57.7 (d, C-12), 57.2 (t, C-27), 55.3 (d, C-13), 54.2 (s, C-4), 41.3 (d, C-6), 40.7 (t, C-2), 37.5 (d, C-8), 31.8 (t, C-14), 31.2 (t, C-9), 28.0 (t, C-11), 23.7 (q, C-23), 23.2 (t, C-10), 19.2 (q, C-21), 16.8 (q, C-22), 15.8 (q, C-25), 13.5 (q, C-24); EIMS m/z 509 [M]⁺ (9), 491 (4), 322 (28), 321 (25), 180 (45), 167 (40), 166 (100), 165 (49), 154 (47), 138 (23); HREIMS m/z 509.2467 (calcd. for $C_{26}H_{39}NO_7S$, 509.2447).

Epothilone $B_{10}$ (9): colorless amorphous solid; $[\alpha]^{22}$ −27 (c 0.15, MeOH); UV (MeOH) $\lambda_{max}$ nm ($\epsilon$) 212 (15800), 247 (12500); IR (KBr) $\nu_{max}$ 3434, 2962, 2930, 2876, 2858, 1733, 1692, 1461, 1259, 1052, 981 cm⁻¹; ¹H NMR (CDCl₃, 600 MHz) δ 6.99 (1H, s, H-19), 6.60 (1H, bs, H-17), 5.42 (1H, dd, J=8.0, 3.0 Hz, H-15), 4.25 (1H, ddd, J=9.5, 6.3, 2.8 Hz, H-3), 4.23(1H, bs, 3-OH), 3.77 (1H, ddd, J=4.0, 3.9, 3.8 Hz, H-7), 3.30 (1H, dq, J=4.0, 6.9 Hz, H-6), 3.01 (2H, q, J=7.6 Hz, H-21), 2.81 (1H, dd, J=7.7, 4.6 Hz, H-13), 2.68 (1H, bs, 7-OH), 2.54 (1H, dd, J=13.9, 9.5 Hz, H-2a), 2.36 (1H, dd, J=13.9, 2.8 Hz, H-2b), 2.11 (1H, ddd, J=15.3, 4.6, 3.0 Hz, H-14a), 2.09 (3H, s, H-27), 1.91 (1H, ddd, J=15.3, 8.0, 7.7 Hz, H-14b), 1.74 (1H, m, H-8), 1.73 (1H, m, H-11a), 1.51 (1H, m, H-10a), 1.41 (1H, m, H-11b), 1.39 (3H, t, J=7.6 Hz, H-28), 1.38 (3H, m, H-9 and H-10b), 1.37 (3H, s, H-23), 1.28 (3H, s, H-26), 1.17 (3H, d, J=6.9 Hz, H-24), 1.09 (3H, s, H-22), 1.01 (3H, d, J=7.0 Hz, H-25); EIMS m/z 521 [M]⁺ (22), 449 (7), 350 (18), 334 (57), 248 (16), 234 (27), 196 (41), 182 (59), 180 (96), 178 (100), 166 (44), 154 (44); HREIMS m/z 521.2808 (calcd. for $C_{28}H_{43}NO_6S$, 521.2811).

Epothilone $G_1$ (10): colorless amorphous solid; $[\alpha]_D^{22}$ −39.7 (c 1.0, MeOH); UV (MeOH) $\lambda_{max}$ nm ($\epsilon$) 203 (15200), 236 (15100); IR (KBr) $\nu_{max}$ 3456, 2962, 2933, 2876, 1736, 1691, 1585, 1466, 1262, 980 cm⁻¹; ¹H NMR (CDCl₃, 400 MHz) δ 7.47(1H, s, H-19), 6.33 (1H, bs, H-17), 5.42 (1H, dd, J=8.3, 2.9 Hz, H-15), 4.11 (1H, ddd, J=10.1, 6.1, 3.4 Hz, H-3), 3.78 (1H, bddd, J=5.2, 3.5, 3.5 Hz, H-7), 3.63 (1H, bd, J=6.1 Hz, 3-OH), 3.21 (1H, dq, J=5.2, 7.0 Hz, H-6), 3.00 (1H, ddd, J=7.7, 4.8, 4.2 Hz, H-13), 2.88 (1H, ddd, J=7.1, 4.2, 4.2 Hz, H-12), 2.53 (1H, dd, J=14.8, 10.1 Hz, H-2a), 2.51 (1H, bd, J=3.5 Hz, 7-OH), 2.43 (1H, dd, J=14.8, 3.4 Hz, H-2b), 2.43 (3H, s, H-21), 2.07 (1H, ddd, J=15.1, 4.8, 2.9 Hz, H-14a), 1.99 (3H, d, J=1.3 Hz, H-27), 1.86 (1H, ddd, J=15.1, 8.3, 7.7 Hz, H-14b), 1.71 (1H, m, H-8), 1.69 (1H, m, H-11a), 1.53 (1H, m, H-10a), 1.42 (1H, m, H-11b), 1.40 (3H, m, H-9 and H-10b), 1.34 (3H, s, H-23), 1.16 (3H, d, J=7.0 Hz, H-24), 1.09 (3H, s, H-22), 0.99 (3H, d, J=6.9 Hz, H-25); ¹³C NMR (CDCl₃, 100 MHz) δ 220.1 (s, C-5), 170.5 (s, C-1), 161.0 (s, C-20), 137.4 (s, C-18), 136.7 (s, C-16), 135.9 (d, C-19), 116.4 (d, C-17), 76.4 (d, C-15), 74.9 (d, C-7), 73.7 (d, C-3), 57.4 (d, C-12), 54.4 (d, C-13), 52.6 (s, C-4), 43.8 (d, C-6), 38.8 (t, C-2), 36.2 (d, C-8), 31.4 (t, C-14), 30.4 (t, C-9), 27.0 (t, C-11), 23.9 (t, C-10), 21.3 (q, C-23), 21.2 (q, C-22), 17.2 (q, C-25), 15.8 (q, C-27), 14.4 (q, C-24), 13.8 (q, C-21); EIMS m/z 477 [M]⁺ (4), 405 (7), 290 (40), 152 (39), 150 (100), 148 (23), 124 (23); HREIMS m/z 477.2684 (calcd. for $C_{26}H_{39}NO_7$, 477.2727).

Epothilone $G_2$ (11): colorless amorphous solid; $[\alpha]_D^{22}$ −22.6 (c 1.0, MeOH); UV (MeOH) $\lambda_{max}$ nm ($\epsilon$) 202 (21500), 236 (14800); IR (KBr) $\nu_{max}$ 3456, 2965, 2934, 2877, 1737, 1690, 1586, 1464, 1250,980 cm⁻¹, ¹H NMR (CDCl₃, 400 MHz) δ 7.48 (1H, s, H-19), 6.33 (1H, bs, H-17), 5.43 (1H, dd, J=7.1, 3.6 Hz, H-15), 4.12 (1H, ddd, J=9.9, 6.4, 3.4 Hz, H-3), 3.77 (1H, ddd, J=4.7, 4.4, 4.1 Hz, H-7), 3.83 (1H, bd, J=6.4 Hz, 3-OH), 3.30 (1H, dq, J=4.7, 6.9 Hz, H-6), 2.78 (1H, dd, J=7.0, 5.4 Hz, H-13), 2.54 (1H, dd, J=14.3, 9.9 Hz, H-2a), 2.51 (1H, bd, J=4.1 Hz, 7-OH), 2.44 (3H, s, H-21), 2.40 (1H, dd, J=14.3, 3.4 Hz, H-2b), 2.03 (1H, ddd, J=15.2, 5.4, 3.6 Hz, H-14a), 2.00 (3H, d, J=1.3 Hz, H-27), 1.92 (1H, ddd, J=15.1, 7.1, 7.0 Hz, H-14b), 1.71 (1H, m, H-8), 1.68 (1H, m, H-11a), 1.51 (1H, m, H-10a), 1.42 (1H, m, H-11b), 1.39 (3H, m, H-9 and H-10b), 1.35 (3H, s, H-23), 1.26 (3H, s, H-26), 1.16 (3H, d, J=6.9 Hz, H-24), 1.07 (3H, s, H-22), 0.99 (3H, d, J=7.0 Hz, H-25); ¹³C NMR (CDCl₃, 100 MHz) δ 220.7 (s, C-5), 170.5 (s, C-1), 161.0 (s, C-20), 137.4 (s, C-18), 136.5 (s, C-16), 135.9 (d, C-19), 116.3 (d, C-17), 76.6 (d, C-15), 74.6 (d, C-7), 73.5 (d, C-3), 61.3 (s, C-12), 61.1 (d, C-13), 52.7 (s, C-4), 43.4 (d, C-6), 39.0 (t, C-2), 36.5 (d, C-8), 32.0 (t, C-11), 31.8 (t, C-14), 30.8 (t, C-10), 22.9 (q, C-26), 21.0 (q, C-23), 20.8 (q, C-22), 17.2 (q, C-25), 15.9 (q, C-27), 14.1 (q, C-24), 13.8 (q, C-21); EIMS m/z 491[M]⁺ (21), 419 (6), 320 (18), 304 (39), 166 (42), 152 (57), 150 (100), 149 (44), 148 (58), 124 (35), 109 (33); HREIMS m/z 491.2878 (calcd. for $C_{27}H_{41}NO_7$, 491.2883).

Epothilone H₁ (12): colorless amorphous solid; $[\alpha]_D^{22}$ −84.2 (c 0.2, MeOH); UV (MeOH) $\lambda_{max}$ nm (ε) 203 (19600), 237 (12000); IR (KBr) $\nu_{max}$ 3436, 2933, 2880, 2860, 1734, 1688, 1585, 1251, 1007 cm⁻¹; ¹H NMR (CDCl₃, 400 MHz) δ 7.47 (1H, s, H-19), 6.31 (1H, bs, H-17), 5.43 (1H, ddd, J=10.6, 10.2, 4.5 Hz, H-12), 5.36 (1H, dddd, J=10.6, 9.6, 5.0, 1.3 Hz, H-13), 5.30 (1H, dd, J=9.9, 2.0 Hz, H-15), 4.16 (1H, ddd, J=11.2, 5.3, 2.8 Hz, H-3), 3.73 (1H, ddd, J=3.9, 2.5, 2.3 Hz, H-7), 3.12 (1H, dq, J=2.3, 6.9 Hz, H-6), 2.92 (1H, d, J=2.5 Hz, 7-OH), 2.91 (1H, d, J=5.3 Hz, 7-OH), 2.66 (1H, ddd, J=15.1, 9.9, 9.6 Hz, H-14a), 2.50 (1H, dd, J=15.4, 11.2 Hz, H-2a), 2.43 (3H, s, H-21), 2.37 (1H, dd, J=15.4, 2.8 Hz, H-2b), 2.23 (1H, m, H-14b), 2.18 (1H, m, H-11a), 2.01 (1H, m, H-11b), 2.08 (3H, d, J=1.3 Hz, H-27), 1.74 (1H, m, H-8), 1.65 (1H, m, H-10a), 1.33 (1H, m, H-9a), 1.31 (3H, s, H-23), 1.19 (1H, m, H-10b), 1.18 (1H, m, H-9b), 1.17 (3H d, J=6.9 Hz, H-24), 1.08 (3H, s, H-22), 0.99 (3H, d, J=7.1 Hz, H-25); ¹³C NMR, see Table 1; EIMS m/z 461 [M]⁺ (6), 310 (5), 274 (10), 273 (7), 171 (63), 152 (100), 148 (18), 111 (15); HREIMS m/z 461.2743 (calcd. for $C_{26}H_{39}NO_6$, 461.2777).

Epothilone H₂ (13): colorless amorphous solid; $[\alpha]_D^{22}$ −44.4 (c 0.25, MeOH); UV (MeOH) $\lambda_{max}$ nm (ε) 203 (14500), 236 (12200); IR (KBr) $\nu_{max}$ 3436, 2967, 2935, 2880, 1734, 1690, 1586, 1251, 1007 cm⁻¹; ¹H NMR (CDCl₃, 400 MHz) δ 7.46 (1H, s, H-19), 6.30 (1H, bs, H-17), 5.23 (1H, dd, J=9.8, 2.1 Hz, H-15), 5.12 (1H, dd, J=10.1, 5.3 Hz, H-13), 4.20 (1H, ddd, J=10.8, 5.7, 2.9 Hz, H-3), 3.71 (1H, ddd, J=3.8, 2.6, 2.6 Hz, H-7), 3.14 (1H, dq, J=2.6, 6.9 Hz, H-6), 2.93 (d, J=5.7 Hz, 3-OH), 2.90 (1H, bd, J=2.6 Hz, 7-OH), 2.62 (1H, ddd, J=15.1, 9.8, 9.8 Hz, H-14a), 2.46 (1H, dd, J=15.1, 10.8 Hz, H-2a), 2.43 (3H, s, H-21), 2.3 (1H, dd, J=15.1, 2.9 Hz, H-2b), 2.29 (1H, m, H-11a), 2.19 (1H, bd, J=15.1 Hz, H-14b), 1.97 (3H, d, J=1.3 Hz, H-27), 1.87 (1H, m, H-11b), 1.73 (1H, m, H-8), 1.67 (1H, m, H-10a), 1.65 (3H, bs, H-26), 1.32 (3H, s, H-23), 1.26 (2H, m, H-9), 1.24 (1H, m, H-10b), 1.18 (3H, d, J=6.9 Hz, H-24), 1.07 (3H, s, H-22), 1.00 (3H, d, J=7.0 Hz, H-25); ¹³C NMR (CDCl₃, 100 MHz), δ 220.6 (s, C-5), 170.3 (s, C-1), 161.0 (s, C-20), 138.6 (s, C-12), 138.4 (s, C-16), 137.5 (s, C-18), 135.6 (d, C-19), 120.8 (d, C-13), 115.8 (d, C-17), 78.9 (d, C-15), 74.3 (d, C-7), 72.7 (d, C-3), 53.3 (s, C-4) 42.0 (d, C-6), 39.6 (t, C-2), 38.6 (d, C-8), 32.4 (t, C-14), 31.9 (t, C-9), 31.6 (t, C-11), 25.6 (t, C-10), 23.0 (q, C-26), 22.8 (q, C-23), 18.8 (q, C-22), 16.1 (q, C-27), 15.9 (q, C-25), 13.8 (q, C-21), 13.6 (q, C-24), EIMS m/z 475 [M]⁺ (11), 288 (9), 287 (5), 188(7), 171 (32), 152 (100), 111 (10); HREIMS m/z 475.2913 (calcd. for $C_{27}H_{41}NO_6$, 475.2934).

Epothilone C₁ (16): colorless amorphous solid; $[\alpha]_D^{22}$ −114.0 (c 10.0, MeOH); UV (MeOH) $\lambda_{max}$ nm (ε) 211 (16500), 248 (12500); IR (KBr) $\nu_{max}$ 3440, 2933, 2877, 2858, 1730, 1708, 1457, 1244,981 cm¹; ¹H NMR (CDCl₃, 300 MHz) δ 6.96 (1H, s, H-19), 6.56 (1H, bs, H-17), 5.47 (1H, dd, J=9.2, 3.0 Hz, H-15), 5.43 (1H, m, H-12), 5.40 (1H, m, H-13), 4.40 (1H, ddd, J=6.2, 6.1, 6.1 Hz, H-3), 3.69 (1H, dd, J=5.7, 3.6 Hz, H-7), 3.01 (1H, dq, J=5.7, 6.9 Hz, H-6), 3.01 (1H, bs, 3-OH), 2.84 (1H, dq, J=5.2, 7.0 Hz, H-4), 2.68 (3H, s, H-21), 2.66 (1H, ddd, J=16.4, 9.2, 7.3 Hz, H-14a), 2.64 (1H, dd, J=15.9, 7.1 Hz, H-2a), 2.54 (1H, dd, J=15.9, 6.1 Hz, H-2b), 2.38 (1H, bd, J=16.4 Hz, H-14b), 2.35 (1H, bs, 7-OH), 2.07 (3H, bs, H-27), 2.03 (2H, m, H-11), 1.62 (1H, m, H-10a), 1.53 (1H, m, H-8), 1.35 (1H, m, H-9a), 1.22 (1H, m, H-9b), 1.19 (3H, d, J=6.9 H, H-24), 1.14 (3H, d, J=6.9 Hz, H-23), 1.10 (1H, m, H-10b), 0.95 (3H, d, J=6.9 Hz, H-25), ¹³C NMR, see Table 1; EIMS m/z 463 [M]⁺ (5), 324 (8), 290 (8), 204 (7), 168 (100), 164 (15), 139 (36); HREIMS m/z 463.2381 (calcd. for $C_{25}H_{37}NO_5S$, 463.2392).

Epothilone D₁ (17): colorless amorphous solid; $[\alpha]^{22}D$ −118.6 (c 0.5, MeOH); UV (MeOH) $\lambda_{max}$ nm (ε) 208 (18300), 249 (11900); IR (KBr) $\nu_{max}$ 3439, 2965, 2934, 2877, 1729, 1707, 1456, 1250, 980 cm⁻¹; ¹H NMR (CDCl₃, 300 MHz) δ 6.98 (1H, s, H-19), 6.56 (1H, bs, H-17), 5.51 (1H, dd, J=9.5, 3.4 Hz, H-15), 5.16 (1H, dd, J=8.0, 4.2 Hz, H-13), 4.42 (1H, ddd, J=7.1, 6.3, 5.5 Hz, H-3), 3.70 (1H, dd, J=6.5, 2.9 Hz, H-7), 3.07 (1H, dq, J=6.5, 6.9 Hz, H-6), 2.95 (1H, dq, J=4.7, 7.0 Hz, H-4), 2.71 (3H, s, H-21), 2.69 (1H, dd, J=16.0, 6.3 Hz, H-2a), 2.64 (1H, m, H-14a), 2.59 (1H, dd, J=16.0, 7.1 Hz, H-2b), 2.46 (1H, bs, 3-OH), 2.38 (1H, bd, J=16.0 Hz, H-14b), 2.19 (1H, ddd, J=13.3, 8.6, 5.7 Hz, H-11a), 2.10 (3H, d, J=1.4 Hz, H-27), 2.02 (1H, bs, 7-OH), 1.91 (1H, ddd, J=13.3, 6.0, 6.0 Hz, H-11b), 1.68 (1H, m, H-10a), 1.66 (3H, bs, H-26), 1.53 (1H, m, H-8), 1.37 (1H, m, H-9a), 1.26 (1H, m, H-9b), 1.24 (3H, d, J=6.9 Hz, H-24), 1.19 (1H, m, H-10b), 1.14 (3H, d, J=7.0 Hz, H-23), 0.99 (3H, d, J=6.9 Hz, H-25); ¹³C NMR (CDCl₃, 100 MHz) δ 217.0 (s, C-5), 169.7 (s, C-1), 165.0 (s, C-20), 152.2 (s, C-18), 138.5 (s, C-12), 137.7 (s, C-16), 120.7 (d, C-13), 120.1 (d, C-17), 116.3 (d, C-19), 78.8 (d, C-15), 77.2 (d, C-7), 67.7 (d, C-3), 52.1 (d, C4), 46.5 (d, C-6), 40.6 (t, C-2), 37.6 (d, C-8), 32.3 (t, C-14), 31.8 (t, C-11), 29.5 (t, C-9), 25.5 (t, C-10), 23.1 (q, C-26), 19.2 (q, C-21), 15.5 (q, C-27), 16.6 (q, C-25), 14.5 (q, C-24), 9.7 (q, C-23); EIMS m/z 477 [M]⁺ (13), 304 (19), 303 (31), 218 (40), 204 (41) 168 (100), 164 (45), 157 (25), 139 (18); HREIMS m/z 477.2544 (calcd. for $C_{26}H_{39}NO_5S$, 477.2549).

Epothilone C₂ (18): colorless amorphous solid; $[\alpha]_D^{22}$ −11.6 (c 10.0, MeOH); UV (MeOH) $\lambda_{max}$ nm (ε) 212 (15500), 249 (12100); IR (KBr) $\nu_{max}$ 3428, 2962, 2929, 2877, 2859, 1734, 1705, 1460, 1251, 982 cm⁻¹; ¹H NMR (CDCl₃, 300 MHz) δ 6.99 (1H, s, H-19), 6.66 (1H, bs, H-17), 5.55 (1H, ddd, J=10.4, 9.2, 6.1 Hz, H-12), 5.38 (1H, ddd, J=10.4, 9.3, 6.2 Hz, H-13), 5.22 (1H, dd, J=8.8, 2.8 Hz, H-15), 4.42 (1H, dddd, J=9.4, 5.6, 4.2, 4.1 Hz, H-3), 3.93 (1H, d, J=5.6 Hz, 3-OH), 3.86 (1H, m, H-7), 3.15 (1H, bs, 7-OH), 3.12 (1H, dq, J=4.2, 7.0 Hz, H-4), 3.00 (1H, dq, J=6.9, 7.0 Hz, H-6), 2.70 (3H, s, H-21), 2.62 (1H, dddd, J=15.1, 9.3, 8.8, 0.8 Hz, H-14a), 2.58 (1H, dd, J=15.4, 9.4 Hz, H-2a), 2.38 (1H, dd, J=15.4, 4.1 Hz, H-2b), 2.31 (1H, dd, J=15.1, 6.2, 2.8 Hz, H-14b), 2.08 (3H, d, J=1.3 Hz, H-27), 2.15 (1H, m, H-11a), 2.04 (1H, m, H-11b), 1.71 (1H, m, H-8), 1.59 (1H, m, H-10a), 1.43 (1H, m, H-9a), 1.31 (1H, m, H-9b), 1.26 (3H, d, J=7.0 Hz, H-24), 1.15 (3H, d, J=7.0 Hz, H-23), 1.11 (1H, m, H-10b), 1.00 (3H, d, J=6.9 Hz, H-25); ¹³C NMR, see Table 1; EIMS m/z 463 [M]⁺ (7), 324 (7), 306 (8), 290 (17), 168 (100), 164 (14), 139 (27); HREIMS m/z 463.2392 (calcd. for $C_{25}H_{37}NO_5S$, 463.2392).

Epothilone D₂ (19): colorless amorphous solid; $[\alpha]_D^{22}$ −12.5 (c 1.0, MeOH); UV (MeOH) $\lambda_{max}$ nm (ε) 210 (15400), 248 (11200); IR (KBr) $\nu_{max}$ 3436, 2965, 2930, 2877, 1732, 1705, 1458, 1253, 980 cm⁻¹; ¹H NMR (CDCl₃, 400 MHz) δ 6.97 (1H, s, H-19), 6.56 (1H, bs, H-17), 5.18 (1H, dd, J=7.9, 4.9 Hz, H-15), 5.18 (1H, ddd, J=9.6, 5.4, 1.0 Hz, H-13), 4.27 (1H, m, H-3), 3.88 (1H, dd, J=5.6, 4.6 Hz, H-7), 3.19 (1H, bs, 3-OH), 3.07 (1H, dq, J=4.3, 7.0 Hz, H-4), 2.95 (1H, dq, J=5.6, 7.0 Hz, H-6), 2.70 (3H, s, H-21), 2.62 (1H, dd, J=14.9, 7.8 Hz, H-2a), 2.56 (1H, ddd, J=14.7, 9.6, 7.9 Hz, H-14a), 2.43 (1H, dd, J=14.9, 5.6 Hz, H-2b), 2.38 (1H, bs, 7-OH), 2.26 (1H, ddd, J=14.5, 5.4, 4.9 Hz, H-14b), 2.19 (1H, ddd, J=13.0, 10.4, 5.4 Hz, H-11a), 2.10 (3H, d, J=1.4 Hz, H-27), 1.95 (1H, ddd, J=13.0, 10.3, 5.3 Hz, H-11b), 1.72 (1H, m, H-S), 1.68 (3H, bs, H-26), 1.61 (1H, m, H-10a), 1.39 (2H, m, H-9), 1.21 (1H, m, H-10b), 1.19 (3H, d, J=6.9 Hz, H-24), 1.17 (3H, d, J=7.0 Hz, H-22), 1.00 (3H, d, J=6.9 Hz, H-25); ¹³C NMR (CDCl₃, 100 MHz) δ 216.8 (s, C-5), 170.4 (s, C-1), 164.9 (s, C-20), 152.3 (s, C-18), 139.8 (s, C-12), 137.5 (s, C-16), 120.5 (d, C-17), 119.2 (d, C-13), 116.3 (d, C-19), 80.0 (d, C-15), 74.3 (d, C-7), 69.7 (d, C-3), 48.6 (d, C-4), 48.4 (d, C-6), 39.9 (t, C-2), 36.6 (d, C-8), 32.2 (t, C-14), 32.7 (t, C-11), 30.9 (t, C-9), 26.0 (t, C-10), 23.6 (q, C-26), 19.2 (q, C-21), 15.4 (q, C-27), 17.1 (q, C-25), 12.4 (q, C-24), 12.7 (q, C-23); EIMS m/z 477 [M]$^+$ (22), 304 (19), 303 (17), 218 (22), 204 (25), 168 (100), 164 (28), 157 (31), 139 (21); HREIMS m/z 477.2545 (calcd. for $C_{26}H_{39}NO_5S$, 477.2549).

Epothilone $C_3$ (20): colorless amorphous solid; $[\alpha]_D^{22}$ −62.1 (c 5.0, MeOH); UV (MeOH) $\lambda_{max}$ nm ($\epsilon$) 212 (16200), 248 (12300); IR (KBr) $\nu_{max}$ 3432, 2928, 2878, 2858, 1736, 1698, 1252, 1040 cm$^{-1}$; $^1$H NMR (CDCl$_3$, 300 MHz) δ 6.95 (1H, s, H-19), 6.56 (1H, bs, H-17), 5.44 (1H, ddd, J=10.9, 10.3, 5.4 Hz, H-12), 5.33 (1H, ddd, J=10.9, 9.3, 4.6 Hz, H-13), 5.23 (1H, dd, J=9.5, 2.2 Hz, H-15), 4.36 (1H, ddd, J=11.3, 5.6, 2.3 Hz, H-3), 4.04 (1H, d, J=5.6 Hz, 3-OH), 3.93 (1H, ddd, J=9.5, 2.3, 1.4 Hz, H-7), 3.56 (1H, bd, J=2.3 Hz, 7-OH), 2.70 (1H, dd, J=18.0, 1.4 Hz, H-6a), 2.67 (3H, s, H-21), 2.61 (1H, ddd, J=15.3, 9.5, 9.3 Hz, H-14a), 2.38 (1H, dd, J=14.3, 11.3 Hz, H-2a), 2.36 (1H, dd, J=18.0, 9.5 Hz, H-6b), 2.28 (1H, bd, J=15.3 Hz, H-14b), 2.12 (1H, m, H-11a), 2.06 (1H, dd, J=14.3, 2.3 Hz, H-2b), 2.03 (3H, d, J=1.3 Hz, H-27), 1.96 (1H, m, H-11b), 1.75 (1H, m, H-8), 1.54 (1H, m, H-10a), 1.26 (1H, m, H-9a), 1.25 (3H, s, H-23), 1.17 (1H, m, H-10b), 1.15 (1H, m, H-9b), 1.03 (3H, s, H-22), 0.91 (3H, d, J=6.8 Hz, H-25); $^{13}$C NMR, see Table 1; EIMS m/z 463 [M]$^+$ (28), 290 (14), 168 (100), 164 (36), 157 (44), 151 (25); HREIMS m/z 463.2379 (calcd. for $C_{25}H_{37}NO_5S$, 463.2392).

Epothilone $C_4$ (21): colorless amorphous solid; $[\alpha]_D^{22}$ −75.6 (c 1.0, MeOH); UV (MeOH) $\lambda_{max}$ nm ($\epsilon$) 212 (17200), 248 (12500); IR (KBr) $\nu_{max}$ 3434, 2974, 2932, 2859, 1735, 1686, 1252, 1046 cm$^{-1}$; $^1$H NMR (CDCl$_3$, 300 MHz) δ 6.96 (1H, s, H-19), 6.60 (1H, bs, H-17), 5.43 (1H, m, H-12), 5.40 (1H, m, H-13), 5.26 (1H, dd, J=9.6, 2.3 Hz, H-15), 4.41 (1H, ddd, J=11.4, 5.8, 2.5 Hz, H-3), 3.78 (1H, m, H-7), 3.70 (1H, bs, 3-OH), 3.46 (1H, d, J=0.9 Hz, 7-OH), 3.01 (1H, dq, J=0.5, 7.0 Hz, H-6), 2.69 (3H, s, H-21), 2.66 (1H, ddd, J=15.3, 9.6, 8.8 Hz, H-14a), 2.47 (1H, dd, J=14.5, 11.4 Hz, H-2a), 2.29 (1H, m, H-14b), 2.25 (1H, dd, J=14.5, 2.5 Hz, H-2b), 2.24 (1H, m, H-11a), 2.07 (3H, d, J=1.4 Hz, H-27), 1.96 (1H, m, H-11b), 1.51 (2H, m, H-8), 1.44 (2H, m, H-10), 1.37 (2H, m, H-9), 1.32 (3H, s, H-23), 1.17 (3H, d, J=7.0 Hz, H-24), 1.07 (3H, s, H-22); $^{13}$C NMR see Table 1; EIMS m/z 463 [M]$^+$ (7), 276 (15), 171 (33), 168 (100), 164 (23), 151 (22), 111 (13); HREIMS m/z 463.2373 (calcd. for $C_{25}H_{37}NO_5S$, 463.2392).

Epothilone $C_5$ (22): colorless amorphous solid; $[\alpha]_D^{22}$ −158.2 (c 0.5, MeOH); UV (MeOH) $\lambda_{max}$ nm ($\epsilon$) 205 (19500), 247 (12700); IR (KBr) $\nu_{max}$ 3447, 2972, 2927, 1737, 1690, 1450, 1252, 1181, 936 cm$^{-1}$; $^1$H NMR (CDCl$_3$, 400 MHz) δ 6.93 (1H, s, H-19), 6.48 (1H, bs, H-17), 5.48 (1H, ddd, J=10.7, 6.2, 6.2 Hz, H-12), 5.39 (1H, m, H-13), 5.37 (1H, m, H-9), 5.34 (1H, dd, J=8.0, 2.3 Hz, H-15), 4.29 (1H, dd, J=6.0, 2.6 Hz, H-7), 4.09 (1H, ddd, J=10.8, 7.1, 2.9 Hz, H-3), 3.59 (1H, d, J=7.1 Hz, 3-OH), 3.17 (1H, dq, J=6.0, 6.9 Hz, H-6), 2.68 (3H, s, H-21), 2.54 (1H, ddd, J=15.2, 8.1, 8.0 Hz, H-14a), 2.44 (1H, bs, 7-OH), 2.42 (1H, dd, J=15.1, 2.9 Hz, H-2a), 2.41 (1H, ddd, J=15.2, 2.3, 2.3 Hz, H-14b), 2.34 (1H, dd, J=15.1, 10.8 Hz, H-2b), 2.20 (1H, m, H-10a), 2.18 (2H, m, H-11), 2.12 (1H, m, H-10b), 2.06 (3H, bs, H-27), 1.67 (3H, bs, H-25), 1.27 (3H, s, H-23), 1.21 (3H, d, J=6.9 Hz, H-24), 1.15 (3H, s, H-22); $^{13}$C NMR, see Table 1; EIMS m/z 475 [M]$^+$ (6), 392 (7), 304 (6), 288 (33), 204 (76), 171 (19), 168 (100), 164 (12); HREIMS m/z 475.2380 (calcd. for $C_{26}H_{37}NO_5S$, 475.2392).

Epothilone $D_5$ (23): colorless amorphous solid; $[\alpha]_D^{22}$ −150 (c 0.2, MeOH); UV (MeOH) $\lambda_{max}$ nm ($\epsilon$) 205 (23300), 248 (13600); IR (KBr) $\nu_{max}$ 3439, 2967, 2927, 1736, 1690, 1451, 1254, 1181, 987 cm$^{-1}$; $^1$H NMR (CDCl$_3$, 400 MHz) δ; 6.94 (1H, s, H-19), 6.51 (1H, bs, H-17), 5.34 (1H, bs, H-9), 5.29 (1H, dd, J=8.0, 2.4 Hz, H-15), 5.16 (1H, dd, J=8.2, 6.2 Hz, H-13), 4.30 (1H, bd, J=4.9 Hz, H-7), 4.19 (1H, ddd, J=10.8, 7.6, 3.0 Hz, H-3), 3.68 (1H, d, J=7.6 Hz, 3-OH), 3.17 (1H, dq, J=4.9, 7.0 Hz, H-6), 2.69 (3H, s, H-21), 2.65 (1H, d, J=2.1 Hz, 7-OH), 2.56 (1H, ddd, J=16.2, 8.2, 8.0 Hz, H-14a), 2.40 (1H, dd, J=15.0, 3.0 Hz, H-2a), 2.39 (1H, bd, J=16.2 Hz, H-14b), 2.34 (1H, dd, J=15.0, 10.8 Hz, H-2b), 2.25 (2H, m, H-10a and H-11a), 2.20 (1H, m, H-10b), 2.17 (1H, m, H-11b), 2.05 (3H, d, J=1.0 Hz, H-27), 1.69 (3H, bs, H-25), 1.68 (3H, bs, H-26), 1.29 (3H, s, H-23), 1.23 (3H, d, J=7.0 Hz, H-24), 1.16 (3H, s, H-22); $^{13}$C NMR, see Table 1; EIMS m/z 489 [M]$^+$ (4), 406 (4), 338 (7), 302 (13), 218 (35), 171 (10), 168 (100), 153 (20), 125 (10); HREIMS m/z 489.2536 (calcd. for $C_{27}H_{39}NO_5S$, 489.2549).

Epothilone $C_6$ (24): colorless amorphous solid; $[\alpha]_D^{22}$ −205.2 (c 1.0, MeOH); UV (MeOH) $\lambda_{max}$ nm ($\epsilon$) 218 (24600), 237 (28800); IR (KBr) $\nu_{max}$ 3435, 2967, 2927, 2882, 1732, 1688, 1465, 1258, 988 cm$^{-1}$; $^1$H NMR (CDCl$_3$, 300 MHz) δ 6.97 (1H, s, H-19), 6.58 (1H, bs, H-17), 6.43 (1H, dd, 15.5, 10.8 Hz, H-11), 6.11 (1H, dd, J=10.8, 10.6 Hz, H-12), 5.75 (1H, ddd, J=15.5, 8.3, 5.6 Hz, H-10), 5.34 (1H, m, H-13), 5.34 (1H, dd, J=9.7, 2.4 Hz, H-15), 4.16 (1H, ddd, J=9.2, 4.9, 4.3 Hz, H-3), 3.74 (1H, ddd, J=2.2, 2.1, 1.7 Hz, H-7), 3.24 (1H, dq, J=2.1, 6.9 Hz, H-6), 3.06 (1H, d, J=2.2 Hz, 7-OH), 2.93 (1H, d, J=4.9 Hz, 3-OH), 2.78 (1H, dddd, J=14.1, 9.9 9.7, 0.7, H-14a), 2.71 (3H, s, H-21), 2.48 (1H, m, H-9a), 2.47 (1H, dd, J=15.5, 9.2 Hz, H-2a), 2.40 (1H, dd, J=15.5, 4.3 Hz, H-2b), 2.38 (1H, bdd, J=14.1, 7.8 Hz, H-14b), 2.11 (3)H, d, J=1.3 Hz, H-27), 1.96 (1H, m, H-8), 1.33 (3H, s, H-23), 1.11 (3H, d, J=6.9 Hz, H-24), 1.06 (3H, H-22), 1.05 (3H, d, J=6.8 Hz, H-25); $^{13}$C NMR, see Table 1; EIMS m/z 475 [M]$^+$ (13), 387 (2), 316 (4), 288 (15), 230 (16), 204 (9), 171 (18), 168 (100), 164 (14), 151 (17); HREIMS m/z 475.2361 (calcd. for $C_{26}H_{37}NO_5S$, 475.2392).

Epothilone $C_7$ (25): colorless amorphous solid; $[\alpha]_D^{22}$ −XXX (c 2.0, MeOH); UV (MeOH) $\lambda_{max}$ nm ($\epsilon$) XXX (XXX), XXX (XXX); IR (KBr) $\nu_{max}$ XXX cm$^{-1}$; $^1$H NMR (CDCl$_3$, 400 MHz) δ 7.01 (1H, s, H-19), 6.66 (1H, bs, H-17), 559 (1H, ddd, J=11.1, 11.1, 3.8 Hz, H-12), 5.40 (1H, dd, J=11.1, 9.2, H-13), 5.03 (1H, d, J=9.3 Hz, H-15), 4.62 (1H, dd, J=9.3, 9.2 Hz, H-14), 4.18 (1H, bd, J=11.0 Hz, H-3), 3.72 (1H, bs, H-7), 3.20 (1H, bs, 3-OH), 3.09 (1H, dq, J=1.9, 6.8 Hz, H-6), 3.00 (1H, bs, 7-OH), 2.69 (3H, s, H-21), 2.47 (1H, dd, J=14.8, 11.0 Hz, H-2a), 2.32 (1H, dd, J=14.8, 2.6 Hz, H-2b), 2.27 (1H, m, H-11a), 2.19 (3H, bs, H-27), 2.13 (1H, m, H-11b), 1.76 ((H, m, H-8), 1.70 (1H, m, H-10a), 1.35 (1H, m, H-9a), 1.32 (3H, s, H-23), 1.23 (1H, m, H-9b), 1.21 (1H, m, H-10b), 1.18 (3H, d, J=6.8 Hz, H-24), 1.08 (3H, s, H-22), 1.00 (3H, d, J=6.9 Hz, H-25); EIMS m/z 493 [M]$^+$ XXX; HREIMS m/z 493.XXX (calcd. for $C_{26}H_{39}NO_6S$, 493.2498).

Epothilone $C_8$ (26): colorless amorphous solid; $[\alpha]_D^{22}$ −75.2 (c 2.5, MeOH); UV (MeOH) $\lambda_{max}$ nm ($\epsilon$) 210 (16800), 248 (17800); IR (KBr) $\nu_{max}$ 3443, 2932, 2881, 1734, 1689, 1465, 1255, 1183, 976 cm$^{-1}$; $^1$H NMR (CDCl$_3$, 300 MHz) δ 6.93 (1H, s, H-19), 6.62 (1H, dd, J=15.6, 0.6 Hz, H-17), 6.49 (1H, dd, J=15.6, 6.6 Hz, H-16), 5.52 (1H, dddd, J=9.5, 6.6, 2.8, 0.6 Hz, H-15), 5.42 (1H, m, H-12), 5.41 (1H, m, H-13), 4.13 (1H, ddd, J=11.0, 5.3, 2.8 Hz, H-3), 3.69 (1H, ddd, J=3.7, 2.8, 2.5 Hz, H-7), 3.11 (1H, dq, J=2.5, 6.8 Hz, H-6), 2.95 (1H, d, J=5.3 Hz, 3-OH), 2.90 (1H, d, J=2.8 Hz, 7-OH), 2.69 (3H, s, H-21), 2.67 (1H, ddd, J=14.9, 9.5, 8.4 Hz, H-14a), 2.48 (1H, dd, J=15.6, 11.0 Hz, H-2a), 2.33 (1H, dd, J=15.6, 2.8 Hz, H-2b), 2.30 (1H, bd, J=14.9 Hz, H-14b), 2.14 (1H, m, H-11a), 2.03 (1H, m, H-11b), 1.71 (1H, m, H-8), 1.63 (1H, m, H-10a), 1.31 (1H, m, H-9a), 1.29 (3H, s, H-23), 1.17 (3H, d, J=6.8 Hz, H-24), 1.16 (1H, m, H-10b), 1.14 (1H, m, H-9b), 1.05 (3H, s, H-22), 0.97 (3H, d, J=7.1 Hz, H-25); $^{13}$C NMR, see Table 1; EIMS m/z 463 [M]$^+$ (21), 310 (10), 276 (21), 171 (83), 154 (100), 150 (27), 111 (18); HREIMS m/z 463.2382 (calcd. for $C_{25}H_{37}NO_5S$, 463.2392).

Epothilone $C_9$ (27): colorless amorphous solid; $[\alpha]_D^{22}$–93.4 (c 1.0, MeOH); UV (MeOH) $\lambda_{max}$ nm ($\epsilon$) 209 (15200), 254 (15700); IR (KBr) $\nu_{max}$ 3416, 2966, 2932, 1736, 1689, 1463, 1249, 1011 cm$^{-1}$; $^1$H NMR (CDCl$_3$, 400 MHz) δ 7.06 (1H, s, H-19), 6.65 (1H, bs, H-17), 6.56 (1H, dd, J=10.6, 4.4 Hz, 27-OH), 5.55 (1H, d, J=6.2 Hz, 3-OH), 5.52 (1H, dd, J=11.6, 2.0 Hz, H-15), 5.44 (1H, dddd, J=11.2, 10.7, 3.1, 1.7 Hz, H-12), 5.35 (1H, dddd, J=11.0, 10.7, 3.9, 1.7 Hz, H-13), 4.47 (1H, ddd, J=12.5, 4.4, 1.3 Hz, H-27a), 4.35 (1H, ddd, J=11.7, 6.2, 2.6 Hz, H-3), 4.20 (1H, ddd, J=12.5, 10.6, 0.9 Hz, H-27b), 3.63 (1H, ddd, J=4.6, 1.8, 0.9 Hz, H-7), 3.24 (1H, d, J=1.8 Hz, 7-OH), 3.13 (1H, dq, J=0.9, 6.8 Hz, H-6), 2.80 (1H, ddd, J=14.8, 11.6, 11.0 Hz, H-14a), 2.71 (3H, s, H-21), 2.40 (1H, dd, J=14.4, 11.7 Hz, H-2a), 2.24 (1H, m, H-11a), 2.06 (1H, dd, J=14.4, 2.6 Hz, H-2b), 2.01 (1H, ddd, J=14.8, 3.9, 2.0 Hz, H-14b), 2.00 (1H, m, H-11b), 1.77 (1H, m, H-8), 1.69 (1H, m, H-10a), 1.35 (1H, m, H-9a), 1.35 (3H, s, H-23), 1.19 (1H, m, H-10b), 1.19 (3H, d, J=6.8 Hz, H-24), 1.18 (1H, m, H-9b), 1.01 (3H, d, J=7.1 Hz, H-25), 0.98 (3H, s, H-22); $^{13}$C NMR, see Table 1; EIMS m/z 493 [M]$^+$ (17), 306 (64), 184 (50), 171 (30), 167 (38), 166 (100), 138 (12); HREIMS m/z 493.2502 (calcd. for $C_{26}H_{39}NO_6S$, 493.2498).

trans-Epothilone $C_1$ (28): colorless amorphous solid; $[\alpha]_D^{22}$–84 (c 0.2, MeOH); UV (MeOH) $\lambda_{max}$ nm ($\epsilon$) 211 (17400), 248 (12900); IR (KBr) $\nu_{max}$ 3433, 2961, 2933, 2879, 1730, 1708, 1457, 1251, 975 cm$^{-1}$; $^1$H NMR (CDCl$_3$, 600 MHz) δ 7.00 (1H, s, H-19), 6.64 (1H, bs, H-17), 5.45 (1H, ddd, J=15.2, 6.5, 6.5 Hz, H-12), 5.42 (1H, dd, J=6.4, 3.7 Hz, H-15), 5.35 (1H, dt, J=15.2, 7.1 Hz, H-13), 4.42 (1H, m, H-3), 3.58 (1H, ddd, J=8.1, 7.9, 2.8 Hz, H-7), 3.24 (1H, m, H-6), 3.14 (1H, dq, J=4.0, 6.9 Hz, H-6), 2.92 (1H, d, J=7.9 Hz, 7-OH), 2.71 (3H, s, H-21), 2.71 (2H, m, H-2), 2.53 (2H, m, H-14), 2.17 (1H, d, J=2.17 Hz, 3-OH), 2.11 (1H, m, H-11a), 2.06 (3H, bs, H-27), 1.93 (1H, m, H-11b), 1.68 (1H, m, H-9a), 1.65 (1H, m, H-10a), 1.33 (1H, m, H-8), 1.26 (3H, d, J=6.8 Hz, H-24), 1.16 (1H, m, H-10b), 1.12 (3H, d, J=6.9 Hz, H-22), 1.07 (1H, m, H-9b), 1.00 (3H, d, J=6.8 Hz, H-25); $^{13}$C NMR, see Table 1; EIMS m/z 463 [M]$^+$ (6), 290 (21), 289 (20), 204 (23), 194 (19), 190 (22), 168 (100), 164 (48), 157 (14), 152 (19), 151 (17), 139 (15), 111 (18), HREIMS m/z 463.2371 (calcd. for $C_{25}H_{37}NO_5S$, 463.2392).

trans-Epothilone $C_2$ (29): colorless amorphous solid; $[\alpha]_D^{22}$–3 (c 1.5, MeOH); UV (MeOH) $\lambda_{max}$ nm ($\epsilon$) 211 (15800), 248 (11900); IR (KBr) $\nu_{max}$ 3435, 2963, 2931, 2878, 1731, 1706, 1457, 1273, 979 cm$^{-1}$; $^1$H NMR (CDCl$_3$, 600 MHz) δ 6.99 (1H, s, H-19), 6.57 (1H, bs, H-17), 5.56 (1H, ddd, J=15.1, 7.4, 7.0 Hz, H-12), 5.41 (1H, dd, J=15.1, 7.0, 6.9 Hz, H-13), 5.41 (1H, dd, J=7.7, 2.8 Hz, H-15), 4.13 (1H, dddd, J=6.7, 6.2, 5.6, 5.1 Hz, H-3), 3.78 (1H, ddd, J=8.2, 6.5, 1.9 Hz, H-7), 3.18 (1H, d, J=5.6 Hz, 3-OH), 3.06 (1H, dq, J=8.2, 7.1 Hz, H-6), 2.98 (1H, dq, J=6.2, 7.0 Hz, H-4), 2.71 (3H, s, H-21), 2.64 (1H, dd, J=15.1, 6.7 Hz, H-2a), 2.54 (1H, dd, J=15.1, 5.1 Hz, H-2b), 2.44 (2H, m, H-14), 2.22 (1H, dddd, J=13.8, 7.0, 6.2, 2.9 Hz, H-11a), 2.10 (3H, d, J=1.1 Hz, H-27), 2.09 (1H, d, J=6.5 Hz, 7-OH), 1.88 (1H, dddd, J=13.8, 10.9, 7.4, 2.9 Hz, H-11b), 1.65 (1H, m, H-8), 1.63 (1H, m, H-10a), 1.56 (1H, dddd, J=12.7, 12.7, 3.9, 3.9 Hz, H-9a), 1.20 (3H, d, J=7.1 Hz, H-24), 1.15 (3H, d, J=7.0 Hz, H-23), 1.13 (1H, m, H-10b), 1.04 (1H, m, H-9b), 1.01 (3H, d, J=7.0 Hz, H-25); $^{13}$C NMR, see Table 1; EIMS m/z 463 [M]$^+$ (13), 290 (11), 190 (10), 168 (100), 164 (20), 157 (26), 139 (17); HREIMS m/z 463.2383 (calcd. for $C_{25}H_{37}NO_5S$, 463.2392).

Epothilone $I_1$ (30): colorless amorphous solid; $[\alpha]_D^{22}$–XXX (c XXX, MeOH); UV (MeOH) $\lambda_{max}$ nm ($\epsilon$) XXX; IR (KBr) $\nu_{max}$ XXX cm$^{-1}$; $^1$H NMR (CDCl$_3$, 300 MHz) δ 6.96 (1H, s, H-19), 6.54 (1H, bs, H-17), 5.49 (1H, ddd, J=10.3, 7.3, 7.3 Hz, H-12), 5.33 (1H, dd, J=8.3, 4.4 Hz, H-15), 5.31 (1H, m, H-13), 4.15 (1H, ddd, J=8.0, 5.0, 4.6 Hz, H-3), 3.80 (1H, m, H-7), 3.21 (1H, dq, J=6.0, 6.9 Hz, H-6), 2.89 (1H, d, J=5.0 Hz, 3-OH), 2.70 (3H, s, H-21), 2.65 (1H, ddd, J=15.8, 8.5, 8.3 Hz, H-14a), 2.42 (2H, m, H-2), 2.35 (1H, m, H-14b), 2.27 (1H, bd, J=3.3 Hz, 7-OH), 2.13 (1H, m, H-11a), 2.09 (3H, d, J=1.2 Hz, H-27), 2.00 (1H, m, H-11b), 1.72 (1H, m, H-8), 1.40 (2H, m, H-10$_\beta$), 1.37 (1H, m, H-9$_\beta$a), 1.36 (2H, m, H-9$_\alpha$), 1.32 (3H, s, H-23), 1.27 (1H, m, H-9$_\beta$b and H-10$_\alpha$), 1.13 (3H, d, J=6.9 Hz, H-24), 1.09 (3H, s, H-22), 0.94 (3H, d, J=6.9 Hz, H-25); $^{13}$C NMR (CDCl$_3$, 75 MHz) δ 221.3 (s, C-5), 171.1 (s, C-1), 164.8 (s, C-20), 152.4 (s, C-18), 137.4 (s, C-16), 133.8 (d, C-12), 124.6 (d, C-13), 120.0 (d, C-17), 116.2 (d, C-19), 78.8 (d, C-15), 74.9 (d, C-7), 74.7 (d, C-3), 51.6 (s, C-4), 43.7 (d, C-6), 38.9 (t, C-2), 34.3 (d, C-8), 31.6 (t, C-14), 29.3 (t, C-9$_\alpha$), 28.6 (t, C-10$_\beta$), 28.2 (t, C-10$_\alpha$), 26.6 (t, C-11), 24.8 (t, C-9$_\beta$), 23.6 (q, C-22), 19.3 (q, C23), 19.3 (q, C-21), 16.5 (q, C-25), 15.5 (q, C-27), 13.7 (q, C-24); EIMS m/z 505 [M]$^+$ XXX; HREIMS m/z 505.XXX (calcd. for $C_{28}H_{43}NO_5S$, 505.XXX).

Epothilone $I_2$ (31): colorless amorphous solid; $[\alpha]_D^{22}$–XXX (c XXX, MeOH); UV (MeOH) $\lambda_{max}$ nm ($\epsilon$) XXX; IR (KBr) $\nu_{max}$ XXX cm$^{-1}$; $^1$H NMR (CDCl$_3$, 300 MHz) δ 6.95 (1H, s, H-19), 6.53 (1H, bs, H-17), 5.40 (1H, m, H-12), 5.38 (1H, dd, J=9.8, 3.3 Hz, H-15), 5.37 (1H, m, H-13), 4.21 (1H, ddd, J=8.6, 3.8, 3.6 Hz, H-3), 3.85 (1H, ddd, J=8.5, 5.8, 2.2 Hz, H-7), 3.18 (1H, dq, J=8.5, 7.0 Hz, H-6), 2.70 (3H, s, H-21), 2.65 (1H, ddd, J=15.2, 9.8, 9.0 Hz, H-14a), 2.51 (1H, d, J=3.6 Hz, 3-OH), 2.37 (2H, m, H-2), 2.32 (1H, bd, J=15.2 Hz, H-14b), 2.09 (3H, d, J=1.3 Hz, H-27), 2.07 (2H, m, H-11), 1.78 (1H, m, H-8), 1.65 (1H, d, J=5.8 Hz, 7-OH), 1.57 (1H, m, H-10$_\beta$a), 1.44 (1H, m, H-10$_\alpha$a), 1.42 (1H, m, H-9$_\beta$), 1.32 (3H, s, H-23), 1.21 (1H, m, H-10$_\beta$b), 1.17 (3H, d, J=7.0 Hz, H-24), 1.13 (2H, m, H-9$_\alpha$), 1.06 (3H, s, H-22), 0.95 (3H, d, J=7.0 Hz, H-25$_\alpha$), 0.91 (3H, d, J=6.5 Hz, H-25$_\beta$), 0.68 (1H, m, H-10$_\alpha$b); $^{13}$C NMR (CDCl$_3$, 100 MHz) δ 220.4 (s, C-5), 171.3 (s, C-1), XXX (s, C-20), 152.4 (s, C-18), 137.6 (s, C-16), 134.5 (d, C-12), 125.3 (d, C-13), 119.6 (d, C-17), 116.2 (d, C-19), 78.6 (d, C-15), 77.2 (d, C-7), 75.0 (d, C-3), 51.0 (s, C-4), 44.6 (d, C-6), 38.2 (t, C-2), 36.9 (t, C-9$_\alpha$), 34.5 (t, C-10$_\alpha$), 32.6 (d, C-8), 32.0 (t, C-14), 30.0 (d, C-9$_\beta$), 27.4 (t, C-11), 26.6 (t, C-10$_\beta$), 25.0 (q, C-22), 21.5 (q, C-25$_\beta$), 19.3 (q, C-21), 17.9 (q, C-25$_\alpha$), 17.7 (q, C-23), 15.8 (q, C-24), 15.6 (q, C-27); EIMS m/z 519 [M]$^+$ XXX; HREIMS m/z 519.XXX (calcd. for $C_{29}H_{45}NO_5S$, 519.XXX).

Epothilone $I_3$ (32): colorless amorphous solid; $[\alpha]_D^{22}$–XXX (c XXX, MeOH); UV (MeOH) $\lambda_{max}$ nm ($\epsilon$) XXX; TR (IKr) $\nu_{max}$ XXX cm$^{-1}$; $^1$H NMR (CDCl$_3$, 400 MHz) δ 6.95 (1H, s, H-19), 6.52 (1H, bs, H-17), 5.32 (1H, dd, J=9.1, 3.0 Hz, H-15), 5.08 (1H, dd, J=8.5, 3.9 Hz, H-13), 4.13 (1H, ddd, J=9.4, 4.3, 3.2 Hz, H-3), 3.81 (1H, m, H-7), 3.18 (1H, dq, J=6.8, 7.0 Hz, H-6), 2.83 (1H, d, J=4.3 Hz, 3-OH), 2.70 (3H, s, H-21), 2.61 (1H, ddd, J=15.8, 9.1, 8.5 Hz, H-14a), 2.43 (1H, dd, J=14.0, 3.2 Hz, H-2a), 2.38 (2H, dd, J=14.0, 9.4 Hz, H-2b), 2.30 (1H, bd, J=15.8 Hz, H-14b), 2.16 (1H, ddd, J=14.1, 8.3, 7.4 Hz, H-11a), 2.08 (3H, d, J=1.0 Hz, H-27), 1.99 (1H, d, J=4.7 Hz, 7-OH), 1.92 (1H, ddd, J=14.1, 6.3, 6.3 Hz, H-11b), 1.82 (1H, m, H-8), 1.67 (3H, s, H-26), 1.51 (1H, m, H-10$_\beta$a), 1.40 (1H, m, H-9$_\beta$), 1.33 (1H, m, H-10$_\beta$b), 1.31 (3H, s, H-23), 1.27 (1H, m, H-10$_\alpha$a), 1.23 (1H, m, H-9$_\alpha$a), 1.16 (3H, d, J=7.0 Hz, H-24), 1.10 (1H, m, H-9$_\alpha$b), 1.07 (3H, s, H-22), 0.95 (3H, d, J=7.0 Hz, H-25$_\alpha$), 0.92 (3H, d, J=6.5 Hz, H-25$_\beta$), 0.75 (1H, m, H-10$_\alpha$b); EIMS m/z 533 [M]$^+$ XXX; HREIMS m/z 533.XXX (calcd. for C$_{30}$H$_{47}$NO$_5$S, 533.XXX).

Epothilone I$_4$ (33): colorless amorphous solid; [α]$_D^{22}$–XXX (c XXX, MeOH); UV (MeOH) λ$_{max}$ nm (ε) XXX; IR (KBr) ν$_{max}$ XXX cm$^{-1}$; $^1$H NMR (CDCl$_3$, 400 MHz) δ 6.95 (1H, s, H-19), 6.53 (1H, bs, H-17), 5.47 (1H, dt, J=11.1, 5.8 Hz, H-12), 5.33 (1H, ddd, J=9.2, 3.9, 0.5 Hz, H-15), 5.33 (1H, m, H-13), 4.09 (1H, dddd, J=9.6, 8.1, 4.5, 3.3 Hz, H-3), 3.83 (1H, m, (H-7), 3.57 (1H, bs, 3-OH), 2.89 (1H, dq, J=7.4, 7.1 Hz, H-6), 2.83 (1H, dq, J=8.1, 7.1 Hz, H-4), 2.70 (3H, s, H-21), 2.64 (1H, m, H-14a), 2.42 (1H, dd, J=14.2, 3.3 Hz, H-2a), 2.43 (1H, dd, J=14.2, 9.6 Hz, H-2b), 2.30 (1H, m, H-14b), 2.10(3H, d, J=1.3 Hz, H-27), 2.09 (2H, m, H-11), 1.81 (1H, m, H-8), 1.74 (1H, bd, J=5.6 Hz, 7-OH), 1.53 (1H, m, H-10$_\beta$a), 1.49 (1H, m, H-9$_\beta$), 1.47 (1H, m, H-10$_\alpha$), 1.27 (1H, m, H-10$_\beta$b), 1.24 (1H, m, H-9$_\alpha$a), 1.17 (3H, d, J=7.1 Hz, H-23), 1.14 (1H, m, H-9$_\alpha$b), 1.08 (3H, d, J=7.1 Hz, H-24), 0.97 (3H, d, J=6.9 Hz, H-25$_\alpha$), 0.91 (3H, d, J=6.5 Hz, H-25$_\beta$), 0.79 (1H, m, H-10$_\alpha$b); $^{13}$C NMR (CDCl$_3$, 100 MHz) δ 217.0 (s, C-5), 170.8 (s, C-1), 164.8 (s, C-20), 152.4 (s, C-18), 137.1 (s, C-16), 134.6 (d, C-12), 124.7 (d, C-13), 120.2 (d, C-17), 116.4 (d, C-19), 78.7 (d, C-15), 76.4 (d, C-7), 71.3 (d, C-3), 50.7 (d, C-4), 50.1 (d, C-6), 40.7 (t, C-2), 38.5 (t, C-9$_\alpha$), 35.5 (t, C-10$_\alpha$), 33.4 (d, C-8), 31.8 (t, C-14), 30.0 (d, C-9$_\beta$), 27.2 (t, C-11), 26.7 (t, C-10$_\beta$), 21.4 (q, C-25$_\beta$), 19.3 (q, C-21), 18.2 (q, C-25$_\alpha$), 15.4 (q, C-27), 14.4 (q, C-24), 13.1 (q, C-23); EIMS m/z 505 [M]$^+$ XXX; HREIMS m/z 505.XXX (calcd. for C$_{28}$H$_{43}$NO$_5$S, 505.XXX).

Epothilone I$_5$ (34): colorless amorphous solid; [α]$_D^{22}$–XXX (c XXX, MeOH); UV (MeOH) λ$_{max}$ nm (ε) XXX; IR (KBr) ν$_{max}$ XXX cm$^{-1}$; $^1$H NMR (CDCl$_3$, 400 MHz) δ 6.97 (1H, s, H-19), 6.52 (1H, bs, H-17), 5.32 (1H, dd, J=7.1, 6.2 Hz, H-15), 5.03 (1H, dd, J=8.4, 5.0 Hz, H-13), 4.05 (1H, dddd, J=7.5, 7.2, 5.9, 4.6 Hz, H-3), 3.91 (1H, m, H-7), 3.17 (1H, d, J=5.9 Hz, 3-OH), 2.94 (1H, dq, J=7.2, 7.1 Hz, H-4), 2.87 (1H, dq, J=6.5, 6.9 Hz, H-6), 2.70 (3H, s, H-21), 2.62 (1H, dd, J=14.6, 4.6 Hz, H-2a), 2.60 (1H, m, H-14a), 2.53 (1H, dd, J=14.6, 7.5 Hz, H-2b), 2.31 (1H, m, H-14b), 2.10 (3H, d, J=1.1 Hz, H-27), 2.10 (1H, m, H-11a), 2.02 (1H, m, H-11b), 1.97 (1H, bd, J=5.6 Hz, 7-OH), 1.84 (1H, m, H-8), 1.66 (3H, s, H-26), 1.55 (1H, m, H-9$_\beta$), 1.49 (1H, m, H-10$_\beta$a), 1.39 (1H, m, H-10$_\beta$b), 1.33 (1H, m, H-10$_\alpha$a), 1.31 (1H, m, H-9$_\alpha$a), 1.15 (3H, d, J=7.1 Hz, H-23), 1.12 (1H, m, H-9$_\alpha$b), 1.11 (3H, d, J=6.9 Hz, H-24), 0.97 (3H, d, J=6.9 Hz, H-25$_\alpha$), 0.94 (1H, m, H-10$_\alpha$b), 0.93 (3H, d, J=6.6 Hz, H-25$_\beta$); EIMS m/z 519 [M]$^+$ XXX; HREIMS m/z 519.XXX (calcd. for C$_{29}$H$_{45}$NO$_5$S, 519.XXX).

Epothilone I$_6$ (35): colorless amorphous solid; [α]$_D^{22}$–XXX (c XXX, MeOH); UV (MeOH) λ$_{max}$ nm (ε) XXX; IR (KBr) ν$_{max}$ XXX cm$^{-1}$; $^1$H NMR (CDCl$_3$, 400 MHz) δ 6.97 (1H, s, H-19), 6.52 (1H, bs, H-17), 5.24 (1H, dd, J=6.9, 6.9 Hz, H-15), 5.02 (1H, dd, J=8.8, 5.2 Hz, H-13), 4.22 (1H, tdd, J=6.1, 5.6, 4.8 Hz, H-3), 3.76 (1H, ddd, J=6.1, 5.7, 5.6 Hz, H-7), 3.13 (1H, d, J=5.6 Hz, 3-OH), 3.05 (1H, dq, J=4.8, 7.0 Hz, H-4), 2.79 (1H, dq, J=5.6, 6.9 Hz, H-6), 2.70 (3H, s, H-21), 2.62 (1H, m, H-14a), 2.57 (2H, d, J=6.1 Hz, H-2a), 2.30 (1H, m, H-14b), 2.08 (3H, d, J=1.0 Hz, H-27), 2.02 (2H, m, H-11), 1.73 (1H, d, J=6.1 Hz, 7-OH), 1.69 (1H, m, H-8), 1.66 (3H, s, H-26), XXX (H9$_\alpha$, H-9$_\beta$, H-10$_\alpha$, H-10$_\beta$), 1.21 (3H, d, J=7.0 Hz, H-22), 1.16 (3H, d, J=6.9 Hz, H-24), 0.94 (3H, d, J=6.9 Hz, H-25$_\alpha$), 0.91 (3H, d, J=6.4 Hz, H-25$_\beta$); EIMS m/z 519 [M]$^+$ XXX; HREIMS m/z 519.XXX (calcd. for C$_{29}$H$_{45}$NO$_5$S, 519.XXX).

Epothilone K (36): colorless amorphous solid; [α]$_D^{22}$–7 (c 0.08, MeOH); UV (MeOH) λ$_{max}$ nm (ε) 212 (16700), 248 (12500); IR (KBr) ν$_{max}$ 3431, 2963, 2927, 2856, 1731, 1712, 1262, 1093, 1021, 802 cm$^{-1}$; $^1$H NMR (CDCl$_3$, 300 MHz) δ 6.95 (1H, s, H-19), 6.51 (1H, bs, H-17), 5.49 (3H, m, H-15, H-13, and H-12), 4.04 (1H, dddd, J=7.9, 7.6, 6.9, 3.3 Hz, H-3), 3.36 (1H, dq, J=6.9, 6.8 Hz, H-6), 2.83 (1H, d, J=7.6 Hz, 3-OH), 2.75 (1H, ddd, J=16.1, 6.6, 3.4 Hz, H-14a), 2.74 (1H, dd, J=15.3, 3.3 Hz, H-2a), 2.71 (3H, s, H-21), 2.58 (2H, m, H-14b and H-8), 2.50 (1H, dd, J=15.3, 7.9 Hz, H-2b), 2.29 (1H, m, H-11a), 2.10 (1H, m, H-11b), 2.09 (3H, d, J=0.7 Hz, H-27), 1.78 (1H, m, H-9a), 1.65 (1H, m, H-10a), 1.48 (1H, m, H-10b), 1.18 (1H, m, H-9b), 1.15 (3H, d, J=6.8 Hz, H-22), 1.03 (3H, d, J=6.5 Hz, H-25); EIMS m/z 405 [M]$^+$ (38), 317 (12), 260 (9), 232 (10), 204 (14), 190 (16), 168 (100), 164 (30), 151 (28); HREIMS m/z 405.XXX (calcd. for C$_{26}$H$_{39}$NO$_5$S, 405.XXX).

(37): colorless amorphous solid; [α]$_D^{22}$–27.5 (c 0.4, MeOH); UV (MeOH) λ$_{max}$ nm (ε) 211 (16100), 247(12100); IR (KBr) ν$_{max}$ 3431, 2967, 2929, 2875, 1704, 1462, 1381, 1010 cm$^{-1}$; $^1$H NMR (CDCl$_3$, 400 MHz) δ 6.94 (1H, s, H-19), 6.55 (1H, bs, H-17), 5.56 (1H, dtt, J=10.8, 7.3, 1.4 Hz, H-12), 5.39 (1H, dtt, J=10.8, 7.3, 1.4 Hz, H-13), 4.17 (1H, t, J=6.6 Hz, H-15), 3.50 (1H, ddd, J=8.7, 2.6, 2.6 Hz, H-7), 3.10 (1H, d, J=2.6, 7-OH), 2.90 (1H, dq, J=2.6, 7.2 Hz, H-6), 2.77 (1H, sep, J=6.9 Hz, H-4), 2.70 (3H, s, H-21), 2.40 (2H, m, H-14), 2.07 (2H, m, H-11), 2.04 (3H, d, J=1.1 Hz, H-27), 1.78 (1H, bs, 15-OH), 1.74 (1H, m, H-9a), 1.50 (1H, m, H-8), 1.46 (1H, m, H-10a), 1.27 (1H, m, H-10b), 1.11 (1H, m, H-9b), 1.094 (3H, d, J=6.9 Hz, H-23), 1.089 (3H, d, J=6.9 Hz, H-22), 1.08 (3H, d, J=7.2 Hz, H-24), 0.82 (3H, d, J=6.7 Hz, H-25); $^{13}$C NMR (CDCl$_3$, 100 MHz) δ 220.5 (s, C-5), 164.6 (s, C-20), 152.9 (s, C-18), 141.5 (s, C-16), 133.4 (d, C-12), 125.0 (d, C-13), 119.2 (d, C-17), 115.6 (d, C-19), 77.2 (d, C-15), 74.9 (d, C-7), 44.9 (d, C-6), 40.0 (d, C-4), 35.5 (d, C-8), 33.5 (t, C-14), 32.3 (t, C-9), 27.9 (t, C-11), 26.9 (t, C-10), 19.2 (q, C-21), 18.6 (q, C-23), 18.1 (q, C-22), 15.6 (q, C-25), 14.4 (q, C-27), 9.3 (q, C-24); EIMS m/z 407 [M]$^+$ (0.1), 204 (0.8), 168 (100), 140 (3.4); HREIMS m/z 407.XXX (calcd. for C$_{23}$H$_{37}$NO$_3$S, 407.XXX).

(38): colorless amorphous solid; [α]$^{22}$$_D$+25.0 (c 0.5, MeOH); UV (MeOH) λ$_{max}$ nm (ε) 212 (17700), 247 (13400); IR (KBr) ν$_{max}$ 3427, 2971, 2933, 2878, 2858, 1709, 1457, 1377, 1186, 1023 cm$^{-1}$; $^1$H NMR (CDCl$_3$, 300 MHz) δ 6.95 (1H, s, H-19), 6.55 (1H, bs, H-17), 5.52 (1H, dtt, J=10.9, 7.2, 1.4 Hz, H-12), 5.39 (1H, dtt, J=10.9, 7.1, 1.2 Hz, H-13), 4.18 (1H, ddt, J=3.4, 0.4, 6.7 Hz, H-15), 2.71 (3H, s, H-21), 2.51 (1H, bq, J=6.8 Hz, H-8), 2.48 (1H, dq, J=17.7, 7.4 Hz, H-6a), 2.41 (1H, dq, J=17.7, 7.2 Hz, H-6b), 2.39 (2H, ddd, J=7.1, 6.7, 1.4 Hz, H-14), 2.06 (2H, ddt, 7.2, 1.2, 7.0 Hz, H-11), 2.05 (3H, d, J=1.4 Hz, H-27), 1.81 (1H, d, J=3.4 Hz, 15-OH), 1.66 (1H, m, H-9a), 1.32 (1H, m, H-9b), 1.31 (2H, m, H-10), 1.06 (3H, d, J=6.9 Hz, H-25), 1.04 (3H, dd, J=7.4, 7.2 Hz, H-24); $^{13}$C NMR (CDCl$_3$, 75 MHz) δ 215.3 (s, C-7), 164.6 (s, C-20), 152.9 (s, C-18), 141.5 (s, C-16), 132.7 (d, C-12), 125.3 (d, C-13), 119.2 (d, C-17), 115.6 (d, C-19), 77.2 (d, C-15), 46.0 (d, C-8), 34.3 (t, C-14), 33.5 (t, C-6), 32.7 (t, C-9), 27.5 (t, C-11), 27.3 (t, C-10), 19.2 (q, C-21), 16.5 (q, C-25), 14.4 (q, C-27), 7.8 (q, C-24); EIMS m/z 335 [M]$^+$ (2), 317 (4), 170 (27), 169 (67), 168 (100), 140 (20); HREIMS m/z 335.1912 (calcd. for C$_{19}$H$_{29}$NO$_2$S, 335.1919).

(39): colorless amorphous solid; [α]$_D^{22}$+26.4 (c 0.27, MeOH); UV (MeOE) λ$_{max}$ nm (ε) 203 (19100), 244 (12500); IR (KBr) ν$_{max}$ 3430, 2970, 2934, 2877, 1710, 1458, 1377, 1184 cm$^{-1}$; $^1$H NMR(CDCl$_3$, 400 MHz) δ 6.94 (1H, s, H-19), 6.55 (1H, bs, H-17), 5.17 (1H, t, J=7.3 Hz, H-13), 4.13 (1H, m, H-15), 2.70 (3H, s, H-21), 2.51 (1H, bq, J=6.8 Hz, H-8), 2.47 (1H, dq, J=17.7, 7.2 Hz, H-6a), 2.41 (1H, dq, J=17.7, 7.2 Hz, H-6b), 2.33 (2H, bdd, J=7.3, 6.8 Hz, H-14), 2.05 (3H, d, J=1.2 Hz, H-27), 2.03 (2H, m, H-11) 1.71 (1H, d, J=3.2 Hz, 15-OH), 1.69 (3H, d, J=1.3 Hz, H-26), 1.62 (1H, m, H-9a), 1.32 (3H, m, H-10 and H-9b), 1.06 (3H, d, J=6.9 Hz, H-25), 1.03 (3H, t, J=7.2 Hz, H-24); EIMS m/z 349 [M]$^+$ (0.7), 331 (1.7), 168 (100), 140 (5.1); HREIMS m/z 349.XXX (calcd. for C$_{20}$H$_{31}$NO$_2$S, 349.XXX).

TAB. 1

Activity of epothilones and compounds (1) to (39) against mouse fibroblasts (L929, IC 50/ng/ml)

| Structural type | Epothilone | | | | |
|---|---|---|---|---|---|
| | A$_Y$ | B$_Y$ | C$_Y$ | D$_Y$ | trans C$_Y$ |
| Starting epothilone | (1) 4 | (2) 1–2 | (14) 50–100 | (15) 20 | — |
| 21-Hydroxy (E&F) | (3) 10 | (4) 1.5 | — | — | — |
| Oxazoles (G&H) | (10) 6 | (11) 1 | (12) 120 | (13) 11 | — |
| (R)-4-Desmethyl (X$_1$) | (5) 20 | — | (16) 200 | (17) 20 | (28) 400 |
| (S)-4-Desmethyl (X$_2$) | (6) 7 | — | (10) 25–30 | (19) 12 | (29) 80 |
| 6-Desmethyl (X$_3$) | — | — | (20) 1500 | — | — |
| 8-Desmethyl (X$_4$) | — | — | (21) 800 | — | — |
| 8,9-Dehydro (X$_5$) | — | — | (22) 1500 | (23) 200 | — |
| 10,11-Dehydro (X$_6$) | — | — | (24) 120 | — | — |
| 14-Hydroxy (X$_7$) | — | — | (25) | — | — |
| 16-Desmethyl (X$_8$) | (7) 20 | — | (26) 250 | — | — |
| 27-Hydroxy (X$_9$) | (8) 100 | — | (27) 200 | — | — |
| 21-Methyl (X$_{10}$) | — | (9) 1.5 | — | — | — |
| Compound | — | — | (36) 180 | — | — |
| Compound | — | — | (37) 50 | — | — |
| Compound | — | — | (38) 2000 | (39) 500 | — |

What is claimed is:

1. An Epothilone of the formula:

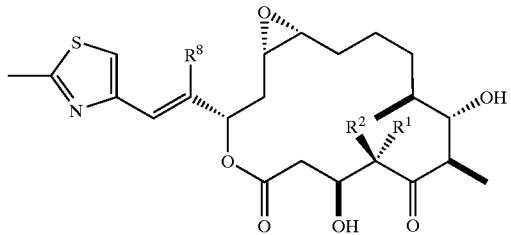

wherein:

for Epothilone A$_1$ R$^1$=H; R$^2$, R$^8$=Methyl;
Epothilone A$_2$ R$^2$=H; R$^1$, R$^8$=Methyl;
Epothilone A$_8$ R$^8$=H; R$^1$, R$^2$=Methyl; or
Epothilone A$_9$ R$^1$=CH$_2$OH; R$^2$, R$^8$=Methyl.

* * * * *